(12) United States Patent
Fujimoto et al.

(10) Patent No.: US 6,540,700 B1
(45) Date of Patent: *Apr. 1, 2003

(54) ULTRASOUND TREATMENT APPARATUS

(75) Inventors: Katsuhiko Fujimoto, Urawa (JP); Satoshi Aida, Otawara (JP); Yoichi Takada, Otawara (JP); Hideki Kosaku, Nasu-gun (JP); Yoichi Hazama, Otawara (JP)

(73) Assignee: Kabushiki Kaisha Toshiba, Kawasaki (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/425,986

(22) Filed: Oct. 25, 1999

(30) Foreign Application Priority Data

| Oct. 26, 1998 | (JP) | ............................................ 10-304080 |
| Dec. 9, 1998 | (JP) | ............................................ 10-350189 |
| Jan. 26, 1999 | (JP) | ............................................ 11-017600 |
| Feb. 25, 1999 | (JP) | ............................................ 11-048330 |

(51) Int. Cl.$^7$ ................................................. A61N 7/02
(52) U.S. Cl. ........................................... 601/3; 600/439
(58) Field of Search ............................. 600/439; 601/2–4

(56) References Cited

U.S. PATENT DOCUMENTS

| 5,080,101 A |   | 1/1992 | Dory |
| 5,150,711 A |   | 9/1992 | Dory |
| 5,358,466 A |   | 10/1994 | Aida et al. |
| 5,553,618 A | * | 9/1996 | Suzuki et al. ................ 600/412 |
| 5,643,179 A | * | 7/1997 | Fujimoto ......................... 601/2 |
| 5,984,881 A | * | 11/1999 | Ishibashi et al. ................ 601/2 |

FOREIGN PATENT DOCUMENTS

| EP | 0 661 029 A1 | * | 7/1995 | ............. A61F/7/00 |
| JP | 10-216145 |   | 8/1998 | |

* cited by examiner

Primary Examiner—Ruth S. Smith
(74) Attorney, Agent, or Firm—Oblon, Spivak, McClelland, Maier & Neustadt, P.C.

(57) ABSTRACT

An ultrasound treatment apparatus includes an ultrasound source for generating treatment ultrasound which is focused, a driving circuit for driving the ultrasound source to generate treatment ultrasound from the ultrasound source, and a controller for controlling to make the driving circuit drive the ultrasound source under an irradiation condition in which an optimization index obtained by the product of the focus intensity (W/cm$^2$), the irradiation period (sec), and the frequency (MHZ) all of the treatment ultrasound falls within an appropriate range from 6,000 (inclusive) to 40,000 (inclusive).

10 Claims, 16 Drawing Sheets

BEFORE
IRRADIATION

AFTER 10-SECOND
IRRADIATION

ULTRASOUND TREATMENT APPARATUS

BACKGROUND OF THE INVENTION

The present invention relates to an ultrasound treatment apparatus for necrosing a tumor such as a tumor by focusing ultrasound on the tumor.

A great deal of attention has recently been given to MIT (Minimally Invasive Treatment). For example, a ESWL (Extracorporeal Shock Wave Lighotriptor (Lighoripsy)) is available, which destroys a calculus by extracorporeally irradiating the calculus with energy instead of a surgical operation. Such energy is generated by a (submerged) discharge type, electromagnetic (induction) type, small-explosion type, piezoelectric type, and the like. The piezoelectric type, in particular, has the following advantages. For example, energy can be focused to a pinpoint spot, no expendable component is required, energy control is easy, and focal position control is easy (Jpn. Pat. Appln. KOKAI Publication No. 60-145131 and U.S. Pat. No. 4,526,168).

In recent years, a less invasive treatment method which focuses on QOL (Quality Of Life) is receiving a great deal of attention. The mainstream of treatment methods for malignant tumors, i.e., cancers, is constituted by surgery, radiotherapy, and chemotherapy. These treatment methods often accompany the hypofunction of an internal organ and a change in the form of the organ. For this reason, even if the patients life is prolonged, the patient must bear a large burden. QOL is the concept that tries to minimize the burden on the patient after treatment by reducing invasion due to the treatment.

One of cancer treatment techniques capable of realizing QOL is thermotherapy, and more specifically, hyperthermia that uses the difference in heat sensitivity between cancer tissue and normal tissue. In hyperthermia, the tumor (target) temperature is kept at about 42.5°, which is the necrosis temperature of a cancer cell. Since the necrosis temperature of normal tissue is slightly higher than that of cancer tissue, the normal tissue is not necrosed.

Heating is performed by various method. If heating is performed by using electromagnetic waves such as microwaves, the electromagnetic waves may be deflected by the electrical characteristics of a living body and may necrose normal tissue around the tumor. In addition, the electromagnetic field can hardly reach the deep tumorous region or deep lying region within a body which depth is more than 5 cm from the skin. As a means for solving this problem, a method of inserting a microwave/RF wave antenna into a portion near a tumor has received a great of attention (Isoda et al., J. Microwave Surgery).

Advantageous characteristics of ultrasound are that no surgical operation is required, energy can be focused to a high degree, energy control is easy, and energy can reach relatively deep (Jpn. Pat. Appln. KOKAI Publication No. 61-139551). Recently, a treatment method of necrosing a tumor accompanying thermal coagulation by instantaneously heating the tumor to 80° C. or more by using very strong ultrasound whose ultrasound intensity reaches several hundred to several thousand $W/cm^2$ at the focus has been developed (G. Vallancien et al.: Progressin Urol, 1991, 1, 84–88, U.S. Pat. No. 5,150,711).

In this treatment method, since ultrasound is focused to a very high degree to form a very small spot, the focus of ultrasound must be moved to entirely treat a large tumor. For this reason, it is required to improve the positioning precision of the focus with respect to the tumor. To improve the positioning precision, the present inventors have developed a technique of imaging the body temperature distribution by using an MRI (Magnetic Resonance Imaging Apparatus) on the basis of the temperature dependency of chemical shift (Jpn. Pat. Appln. KOKAI Publication No. 5-253192). In addition, a technique of imaging the intensity distribution of treatment ultrasound by receiving the echoes of the treatment ultrasound generated by a treatment ultrasound source with an imaging probe has been developed (U.S. Pat. Nos. 1,851,304, 1,821,772, and 1,765,452). An improvement in positioning precision can be attained by using various techniques, as described above.

In addition to an improvement in positioning precision, another challenge for ultrasound treatment is optimization of the amount of energy injected (ultrasound intensity× irradiation period). According to the experiment conducted by the present inventors, injection of excessive energy causes destruction of a tissue cell beyond thermal degeneration. In a thermal degenerate state, the tissue cell is necrosed, but it maintains its form. If, however, the tissue cell is destroyed, its original form changes. For this reason, a tumor or neighboring blood vessels may be damaged. As one method of solving this problem, the present inventors have proposed a phase difference driving method of decreasing the ultrasound intensity (focus intensity) at a focus and widening the acoustic field (Japanese Patent Application Nos. 10-278684 and 10-279088). However, optimization rules for focus intensity and irradiation periods could not be established.

As is known, ultrasound energy is absorbed at an acoustic impedance boundary. For this reason, a portion exhibiting a large difference in acoustic impedance, e.g., the body surface of a patient, is unintentionally heated, and may be burnt. There are no appropriate countermeasures against such situations.

Often, a portion near a focus is scanned with an imaging ultrasound probe to acquire B-mode images near the focus so as to check the progress of treatment while strong treatment ultrasound is irradiated. Typically, the frequency of the strong treatment ultrasound is set to 1.6 MHz, whereas the driving frequency of the imaging ultrasound probe is set to 3.7 to 5.0 MHz. The main components of strong treatment ultrasound echoes are not received by the vibrator of the imaging ultrasound probe. However, harmonic components of the echoes are received as noise by the vibrator of the imaging ultrasound probe. Since the noise is much higher in intensity than the imaging ultrasound, the resultant B-mode image becomes almost white. This makes it difficult to observe the tumor.

As a means for solving this problem, Jpn. Pat. Appln. KOKAI Publication Nos. 60-241436, 60-241436, and 10-216145 disclose a technique of stopping irradiation of treatment ultrasound at predetermined intervals, and executing scanning operation using imaging ultrasound only during the stop periods, thereby acquiring B-mode images without noise.

On the other hand, the operator can use almost white B-mode images to visually check whether treatment ultrasound is really irradiated. If, however, scanning operation using imaging ultrasound is executed only during stop periods of treatment ultrasound, the operator cannot visually check whether the treatment ultrasound is really irradiated, although B-mode images without noise can be acquired.

In the arrangements disclosed in Jpn. Pat. Appln. KOKAI Publication Nos. 60-241436 and 10-216145, a control signal must be directly input from an ultrasound treatment apparatus to an ultrasound transmitting/receiving section of an ultrasound image diagnostic apparatus or an output must be directly extracted from the ultrasound treatment apparatus. For this reason, if at least a conventional ultrasound treatment apparatus is to be used, the ultrasound transmitting/ receiving section inside the apparatus must be modified, or the ultrasound treatment apparatus and the ultrasound image diagnostic apparatus must be integrated. When image information is to be loaded from various image diagnostic apparatuses, e.g., an X-ray image diagnostic apparatus, X-ray CT apparatus, and MRI apparatus, other than an ultrasound treatment apparatus, it is difficult to make modifications for loading of image information with respect to various image diagnostic apparatuses to be combined.

BRIEF SUMMARY OF THE INVENTION

It is an object of the present invention to perform safe, appropriate medical treatment by using an ultrasound treatment apparatus.

According to the present invention, medical treatment is performed under an irradiation condition in which an optimization index obtained by the product of the focus intensity (W/cm$^2$) of treatment ultrasound, the irradiation period (sec) of the treatment ultrasound, and the frequency (MHz) of the treatment ultrasound falls within the appropriate range of 6,000 (inclusive) to 40,000 (inclusive).

According to the present invention, since an irradiation condition is determined on the basis of the focus intensity of treatment ultrasound and the ultrasound intensity in a hyper Echoic region including the body surface of a patient, both optimization of treatment for a tumor and a reduction in damage to the body surface and the like can be attained.

According to the present invention, treatment ultrasound is alternately generated and stopped, and scanning with imaging ultrasound is continuously repeated. B-mode image data sequentially obtained by repetitive scanning are displayed as moving images in real time. B-mode image data corresponding to stop periods of treatment ultrasound are picked up from the B-mode image data sequentially obtained by this repetitive scanning. These picked-up B-mode image data are displayed as skip images. Since a B-mode image during a stop period of treatment ultrasound has an appropriate intensity, the tissue form can be observed. In contrast to this, a B-mode image during a generation period of treatment ultrasound has an excessively high intensity, and hence looks completely white. This makes it impossible to see any tissue form, but allows the operator to determine that treatment ultrasound is indeed irradiated.

In the present invention, treatment ultrasound is alternately generated and stopped, and scanning with imaging ultrasound is intermittently executed in synchronism with stop periods of the treatment ultrasound. Some of scanning periods overlap the generation periods of treatment ultrasound. Therefore, a B-mode image partly looks completely white to hinder the operator from seeing any tissue form. This, however, allows the operator to determine that treatment ultrasound is actually irradiated. In contrast to this, the remaining part of the B-mode image is obtained during a stop period of the treatment ultrasound, and hence is displayed with an appropriate intensity. This allows the operator to observe the tissue form.

According to the present invention, treatment ultrasound is alternately generated and stopped, and scanning with imaging ultrasound is continuously repeated. B-mode image data corresponding to scanning periods which partly overlap stop periods of treatment ultrasound are picked up from the sequentially obtained B-mode image data. Part of a B-mode image therefore looks completely white, and hence does not allow the operator to see any tissue form. This, however, allows the operator to determine that treatment ultrasound is actually irradiated. The remaining part of the B-mode image is obtained during a stop period of the treatment ultrasound, and hence is displayed with an appropriate intensity. This allows the operator to observe the tissue form.

The treatment apparatus of the present invention continuously and externally inputs B-mode image data associated with a cross-section including the focus of treatment ultrasound, picks up B-mode image data corresponding to stop periods of the treatment ultrasound, and displays the data as skip images.

The treatment apparatus of the present invention continuously and externally inputs B-mode image data associated with a cross-section including the focus of treatment ultrasound, picks up the intensity of the focus from the B-mode image data, and displays the intensity as a change over time. The operator can monitor the progress of treatment from this change in intensity over time.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Preferred embodiments of the present invention will be described in detail below with reference to the views of the accompanying drawing.

(First Embodiment)

Figure 1:
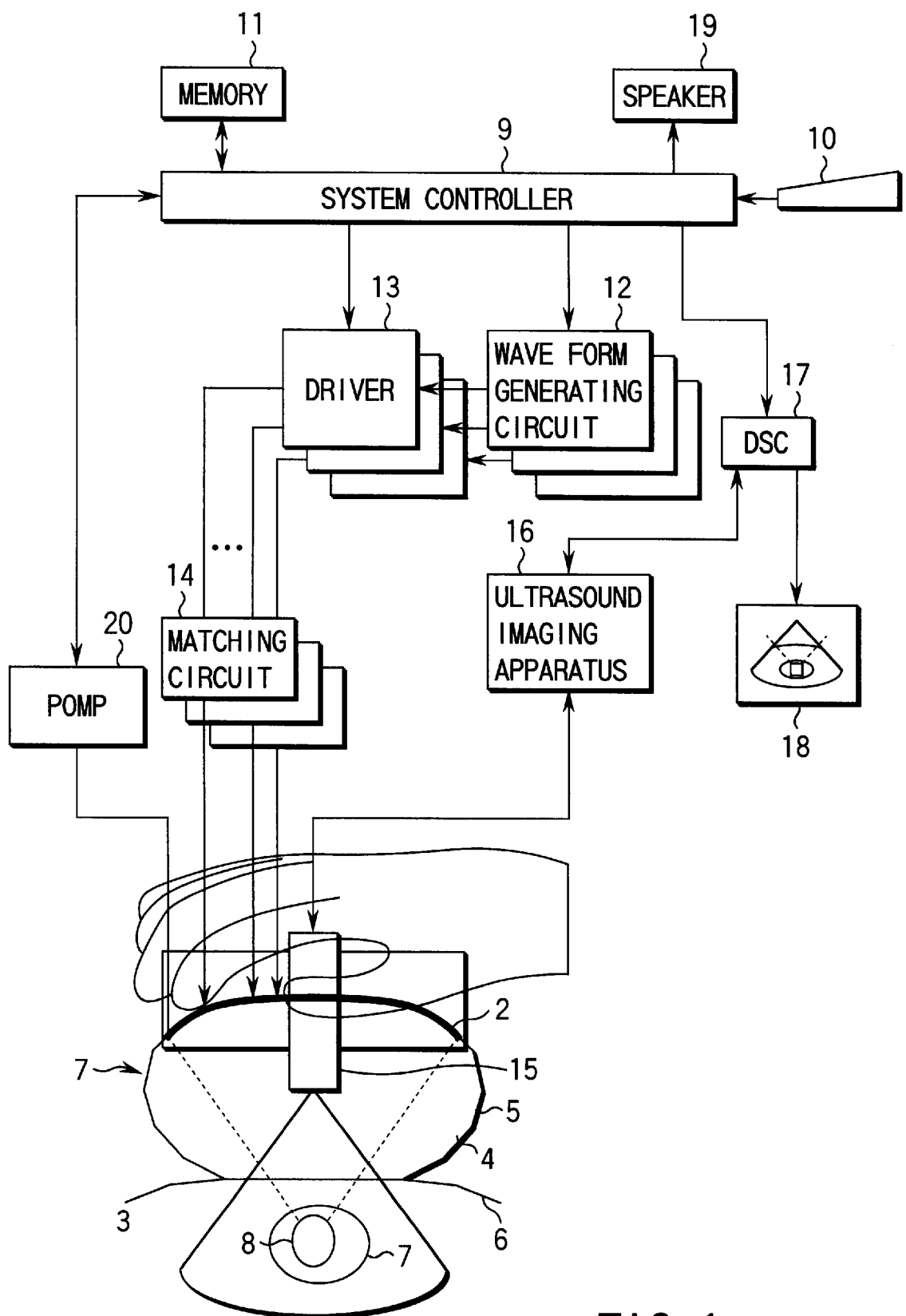
FIG. 1 is a block diagram showing the arrangement of an ultrasound treatment apparatus according to the first embodiment of the present invention.

FIG. 1 shows the arrangement of an ultrasound treatment apparatus according to the first embodiment. An applicator 1 has a treatment ultrasound source 2 for generating strong treatment ultrasound. The treatment ultrasound source 2 has a plurality of piezoelectric elements each having upper and lower electrodes. The plurality of piezoelectric elements are systematically arranged toward a focus.

A hole is formed near the center of the treatment ultrasound source 2, and an imaging ultrasound probe (inner probe) 15 for acquiring a B-mode image (B-mode image (form image)) associated with a cross-section including the focus is inserted in this hole. An operator positions a focus 8 on a tumor 7 and checks the progress of treatment while referring to the B-mode image acquired by an ultrasound imaging apparatus 16 through the imaging ultrasound probe 15 and including a tumor (tumor) 7 displayed on a CRT 18.

Since a mark indicating the position of the focus 8 of the treatment ultrasound source 2 is synthesized with this B-mode image by a digital scan converter 17, the operator can relatively easily position the applicator 1 by manually moving it to align the focus mark with the tumor 7 of a patient 3. The operator can finally confirm on the B-mode image obtained by the ultrasound imaging apparatus 16 that the focus 8 is aligned with the tumor 7.

With recent great reductions in the size and weight of the applicator 1, a hand-held type (portable) applicator like the one shown in FIG. 1 can be implemented. However, the applicator 1 may be supported by a conventional support mechanism with a balancer function to be freely moved or may be motorized.

When the applicator 1 is to be moved, the distance from a tumor surface 6 to the focus 8 must be changed by adjusting the amount of coupling liquid 4 in the applicator 1 using a water circuit (pump) 20. In general, in this liquid amount adjustment, the operator determines the amount of liquid by operating a console panel 10 by himself/herself. If the tumor depth from the tumor surface 6 to the tumor 7 is known, liquid amount adjustment or the like may be automatically controlled in accordance with a command from a system controller 9 by designating the tumor depth. Adjustment of this tumor depth may be performed by attaching/detaching a coupler, acoustic lens, or the like so as to change the depth of focus instead of adjusting the amount of coupling liquid. If the focus 8 can be electronically scanned by phase control, the above tumor depth adjustment may be performed by changing the driving phases between the piezoelectric elements.

The coupling liquid 4 is sealed with a coupling film 5 on the ultrasound irradiation side of the treatment ultrasound source 2 to guide the treatment ultrasound generated by the treatment ultrasound source 2 to the body surface of the patient 3 with little attenuation. In treatment, the coupling film 5 is brought into contact with the tumor surface 6 of the patient 3 through ultrasound jelly (or the like).

When the operator operates the console panel 10 or an irradiation start switch mounted on the applicator 1 upon positioning the applicator 1 while referring to a B-mode image, the system controller 9 controls a wave form generating circuit 12 and driver 13. with this operation, the wave form signal generated by the wave form generating circuit 12 is amplified by the driver 13 and supplied to each piezoelectric element of the treatment ultrasound source 2 through an impedance matching circuit 14. As a consequence, treatment ultrasound is irradiated upon mechanical vibrations of the piezoelectric elements.

A type of optimizing the irradiation condition, which is one of the important features of this embodiment, will be described next. This irradiation condition includes an irradiation period t (sec) and driving electric power P (W) supplied from the driver 13 to each piezoelectric element per unit time. The driving electric power P (W) is determined by an ultrasound intensity (focus intensity) $I_F$ (W/cm$^2$) at the position of the focus 8, an ultrasound attenuation coefficient in the living body, and the like. Information required for the system controller 9 to calculate and determine this optimal irradiation condition is stored in a memory 11 in advance.

This required information includes a resonance frequency f intrinsic to a piezoelectric element 102 and a parameter representing a correlation between the driving electric power intrinsic to the treatment ultrasound source 2 and the focus intensity (a correlation between the unit driving electric power in water and the focus intensity at a unit depth (1 cm).

The required information further includes an upper limit value $E_{MAX}$ of optimization indexes (frequency/energy densities) within which over-irradiation (cell destruction) does not occur and a lower limit value $E_{MIN}$ within which under-irradiation (non-thermal degeneration) does not occur. These values are intrinsic to an internal organ. If, therefore, the irradiation condition is set such that the optimization index falls within the range from the lower limit value $E_{MIN}$ to the upper limit value $E_{MAX}$ (appropriate range), the tumor degenerates without causing any cell destruction in the tumor. That is, thermal degeneration of the tumor can be properly caused.

The required information also includes an upper limit value $I_{FMAX}$ of the focus intensity $I_F$ and an ultrasound attenuation coefficient α of each internal organ. These pieces of required information are stored in a memory 11 in correspondence with the respective internal organs.

The upper limit value $E_{MAX}$ and lower limit value $E_{MIN}$ of a frequency/energy density and the upper limit value $I_{FMAX}$ of the focus intensity $I_F$ are determined for each internal organ experimentally, empirically, and by simulation. For example, for the liver, the upper limit value $E_{MAX}$ of the frequency/energy density is determined to be 40,000; the lower limit value $E_{MIN}$ of the frequency/energy density, 6,000; and the upper limit value $I_{FMAX}$ of the focus intensity $I_F$, 2,000.

The above frequency/energy density is an index (optimization index) newly introduced by the present invention. This value is given by the product of the focus intensity $I_F$, irradiation period (sec), and driving frequency (MHz). This frequency/energy density exhibits a very high correlation with the thermal degeneration state of a tumor. A proper irradiation condition under which desired thermal degeneration can be caused in focus tissue and no cell destruction occurs in surrounding tissue can be effectively determined on the basis of this frequency/energy density.

A procedure by which the system controller 9 determines an appropriate irradiation condition (irradiation period t and driving electric power P) will be described next. This determination procedure can be divided into two stages, i.e., the determination stage for the focus intensity $I_F$ and irradiation period t and the determination stage for the driving electric power P. The determination stage for the focus intensity $I_F$ and irradiation period t will be described first. Of the focus intensity $I_F$ and irradiation period t, the irradiation period t is generally determined by the operator in many cases. For this reason, the procedure for determining the focus intensity $I_F$ will be described first.

When the operator inputs the irradiation period t and information indicating a target internal organ through the console panel 10, the upper limit value $E_{MAX}$ of the frequency/energy density linked to the target internal organ, the lower limit value $E_{MIN}$ of the frequency/energy density linked to the target internal organ, and the upper limit value $I_{FMAX}$ of the focus intensity $I_F$ linked to the target internal organ are loaded from the memory 11 into the system controller 9, together with the driving frequency f intrinsic to the applicator 1.

The system controller 9 determines the appropriate range of the focus intensity $I_F$ so as to satisfy $$E_{MIN} \leq \text{frequency·energy density} \leq E_{MAX}$$

Figure 2:
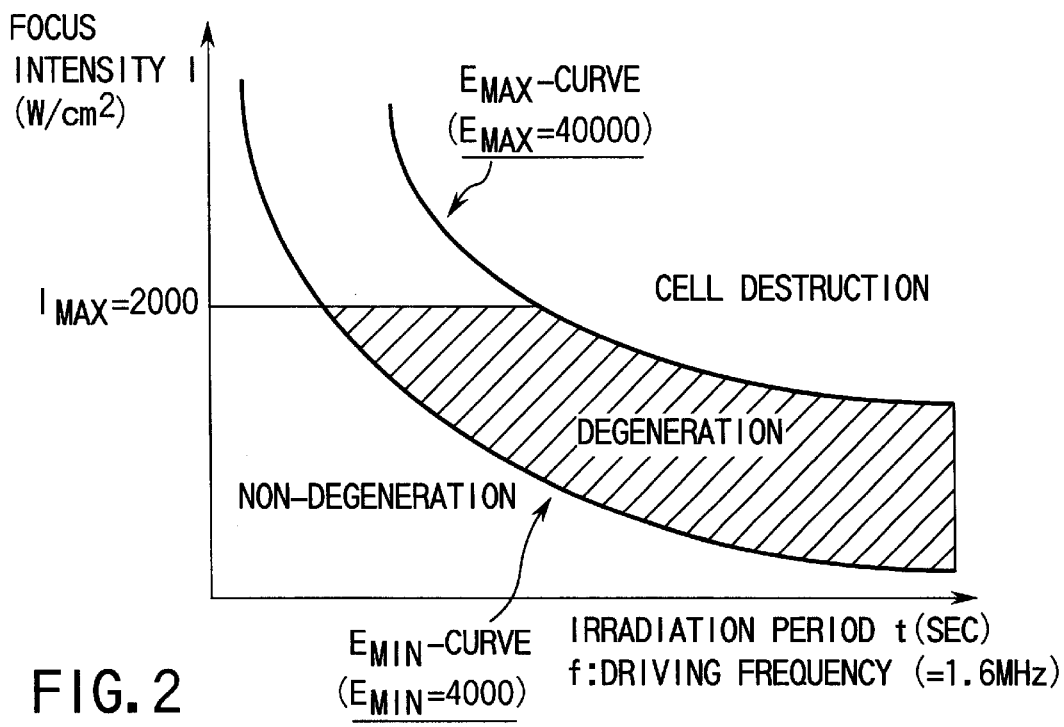
FIG. 2 is a graph showing the appropriate range of an irradiation condition according to the first embodiment.

That is, $$E_{MIN} \leq \text{focus intensity } I_F(\text{W/cm}^2) \times \text{irradiation period } t(\text{second}) \times \text{driving frequency } f(\text{MHZ}) \leq E_{MAX} \quad (1)$$

and the upper limit value $I_{FMAX}$ of the focus intensity $I_F$. Proper medical treatment can be performed within the determined appropriate range of the focus intensity $I_F$. In practice, a substantially median value in the appropriate range is determined as the appropriate focus intensity $I_F$. FIG. 2 shows changes in focus intensity I within the appropriate range over the irradiation period t.

Note that the operator may determine the focus intensity $I_F$ in advance, and the system controller 9 may determine the appropriate irradiation period t. In this case as well, the appropriate range of the irradiation period t is determined according to relation (1), and the median value in the range is determined as the appropriate irradiation period t. In general, for example, in the case of the liver, the focus intensity at the focus 8 is set to 1,000 W/cm² ($\leq I_{FMAX}$=2,000), and the driving frequency is assumed to be 1.6 MHz. According to the experiment conducted by the present applicants, in the case of the liver, the upper limit value $E_{MAX}$ of the frequency/energy density was 40,000, and the lower limit value $E_{MIN}$ of the frequency/energy density was 6,000.

Under this assumption, it suffices if the irradiation period t satisfies $$6{,}000 \leq 1{,}000 \text{ (W/cm}^2) \times \text{irradiation period(second)} \times 1.6 \text{ (MHz)} \leq 40{,}000 \quad (2)$$

Therefore, proper medical treatment can be performed within the range of about 4 sec to about 25 sec. In practice, in consideration of upper and lower margins, a substantially median value in this range, i.e., about 15 sec, is provided as an appropriate irradiation period. This value is in good agreement with the result obtained by the tests conducted on animals by the present inventors.

A method of determining an appropriate value of driving electric power to be supplied from the driver 13 to each piezoelectric element will be described next. Since this driving electric power can be optimized by using the conventional method without any change, this method will be briefly described below by taking the liver as an example. In the case of the liver, the ultrasound attenuation coefficient α is about 0.7 dB/MHz/cm. The driving frequency of ultrasound is set to 1.6 MHz as in the above case.

The focus intensity is attenuated, for every depth of 1 cm, to $$10(-0.7 \times 1.6 \text{ MHz}-(1 \text{ cm}/10)=0.773 \quad (3)$$

Since the focus intensity I must be kept constant for every depth, the driving electric power must be increased by about 1.3 times for every depth of 1 cm. According to this estimation, assuming that the ultrasound intensity at a depth of 1 cm with a driving electric power of 2,000 W becomes 1,000 W/cm² as a correlation parameter between the unit driving electric power P in water and the ultrasound intensity at a unit depth (1 cm), in order to obtain an appropriate ultrasound intensity at a depth of 5 cm, the driving electric power given by $$2000/10^{(-\alpha \times 1.6 \text{ } MHz \times (5-1) \text{ } cm/10)} = 560 \text{ W} \quad (4)$$

is determined as an appropriate value.

As described above, in the case of the liver, an irradiation period of 15 sec and a driving electric power of 560 W are calculated as appropriate values for proper medical treatment at a depth of focus of 5 cm. The system controller 9 performs such calculations to irradiate ultrasound with values corresponding to a treatment target and the characteristics of the target. This makes it possible to perform safe, reliable medical treatment.

Although the operator may input a numerical value as a tumor depth through the console panel 10, semiautomatic control may be performed to make the system controller 9 calculate the distance between the focus and the contact surface between the body surface and the coupling film as a tumor depth when the operator designates the tumor (tumor) 7, together with the contact surface, on a B-mode image. Furthermore, full-automatic control may be performed to make the system controller 9 automatically extract a body surface and tumor (tumor) from a B-mode image by image processing and calculate the distance between the body surface and the tumor as a tumor depth. This calculation can be automated by the following method. The distance from the treatment ultrasound source 2 to the body surface can be approximated from the amount of coupling liquid 4 injected. In the applicator 1 of the type in which the distance (focal length) from the treatment ultrasound source 2 to the focus is fixed, therefore, the tumor depth can be calculated by subtracting the distance from the treatment ultrasound source 2 to the body surface from the focal length.

As described above, at a depth of focus of 5 cm, an irradiation period of 15 sec and a driving electric power of 560 W are calculated as appropriate values for proper medical treatment. The system controller 9 performs such calculations to irradiate ultrasound with values corresponding to a treatment target and the characteristics of the target, thus realizing safe, reliable medical treatment.

Figure 3A:
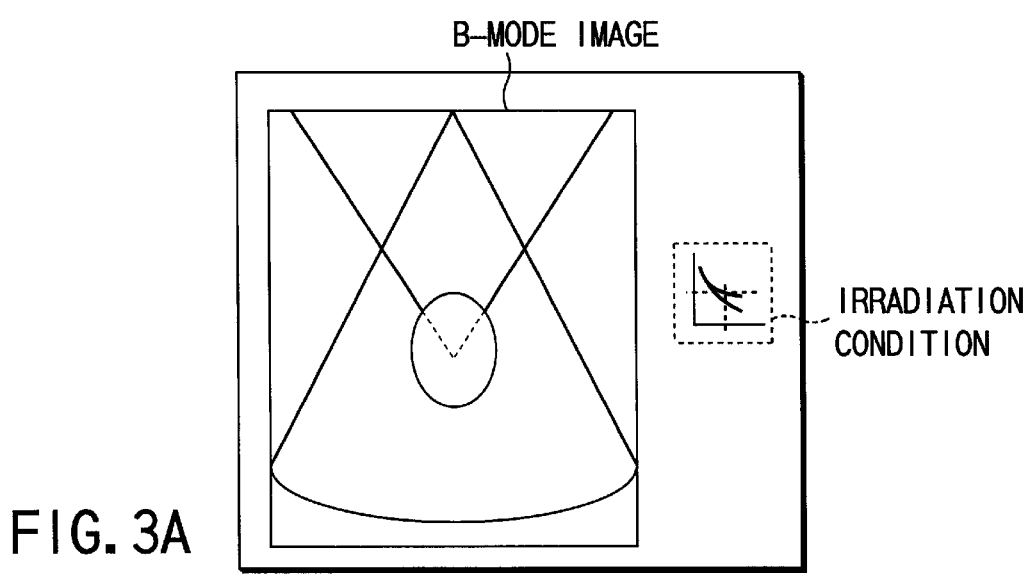
FIG. 3A is a view showing an example of display of an irradiation condition in the first embodiment.
Figure 3B:
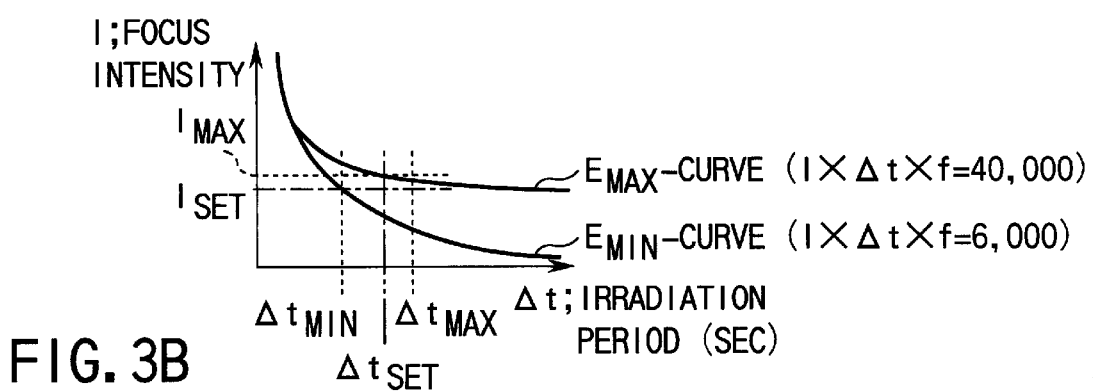
FIG. 3B is a graph showing the details of the display of the irradiation condition in FIG. 3A.

In setting such a treatment condition, the irradiation condition set is graphically displayed, as shown in FIGS. 3A and 3B. The operator can therefore easily set or adjust (correct) the irradiation condition by manual operation.

As described above, according to this embodiment, the following effects can be obtained. The product of an ultrasound intensity (focus intensity) (W/cm$^2$), irradiation period (sec), and driving frequency (MHz) at the focal position in the living body, i.e., the frequency/energy density, has a high correlation with the degeneration state of a tumor. For this reason, a proper irradiation condition under which desired thermal degeneration can be caused in focus tissue and no damage is caused to the surrounding tissue can be finely determined on the basis of the frequency/energy density. This makes it possible to sufficiently treat the tumor without producing any side effect due to an excessive focus intensity, thus allowing safe, efficient irradiation treatment.

In addition, the values ($I_{MAX}$, $E_{MAX}$, $E_{MIN}$) are not influenced much by the size of the focus 8. This embodiment can therefore properly cope with a case wherein irradiation treatment is performed while the focus size is changed, as disclosed in Japanese Patent Application Nos. 10-278684 and 10-279088 and Japanese Patent Nos. 2036277 and 2576427. In this case, if changes in the maximum intensity of ultrasound with changes in focus size are stored in the memory 11 or the like in advance, the irradiation intensity can be set by reading out an intensity value corresponding to the driving method used.

Assume that the system controller 9 monitors irradiation of treatment ultrasound, and detects that at least one of the following cases has occurred: a case wherein the frequency/energy density at the focal position falls outside the range of the upper and lower limit values of frequency/energy densities selectively read out from the memory 11; and a case wherein the ultrasound intensity at the focal position exceeds the upper limit value of ultrasound intensities selectively read out from the memory 11. In this case, a control signal (inhibit signal) for urgent stop may be sent to the driver 13 to urgently stop irradiation of treatment ultrasound or a specific sound or buzzer sound indicating the occurrence of the above event may be generated as a warning (alarming) through a speaker 19. Alternatively, a graphic signal may be sent to the CRT 18 through the digital scan converter 17 to display a specific message indicating the occurrence of the above event on the screen. One, two, or all of these operations, i.e., urgently stopping irradiation, generating a warning, and displaying a message, may be executed.

In the above description, the upper limit values and the like of frequency/energy densities are linked with internal organs. However, the irradiation condition may be further optimized by determining the upper and lower limit values of frequency/energy densities and the upper limit value of focus intensities more finely in accordance with each individual internal organs and the progress of a symptom and linking them with each other.

According to the above description, information such as the upper limit value of frequency/energy densities which is required to allow the system controller 9 to determine an appropriate irradiation condition are stored in the memory 11 in advance, and the system controller 9 calculates appropriate values on the basis of the information. Appropriate irradiation conditions calculated by the above determination method in advance may be stored in the memory 11, and an appropriate irradiation condition may be read out in accordance with an input condition such as information indicating an internal organ.

In addition, the attenuation characteristics of a path and other ultrasound characteristics may be measured or estimated by a means for acquiring ultrasound image and other data, and the condition may be set on the basis of the characteristic values.

The irradiation condition set in the above manner is a condition in a case wherein the focal position is fixed, and ultrasound is continuously irradiated. However, by sequentially updating the irradiation condition, this embodiment can be applied to a case wherein medical treatment is performed while the focus is moved in a wide range. When ultrasound is intermittently irradiated at multiple points instead of being continuously irradiated, since energy has been partly conducted by preceding irradiation owing to thermal conduction and the like, treatment ultrasound can be driven with the value obtained by subtracting the value of the conducted energy (energy density per unit volume) from the total energy.

Only the ultrasound treatment apparatus has been described above. However, the present invention can be applied to other types of treatment methods, e.g., a method of using microwaves to heat/treat a tumor by using energy absorption in tissue.

According to the present invention, the following effect can be obtained. The product of an ultrasound intensity (W/cm$^2$) at a focal position in the living body, irradiation period (sec), and driving frequency (MHz) exhibits a high correlation with thermal degeneration of the tumor. For this reason, an irradiation condition under which desired thermal degeneration can be caused in focus tissue and no damage is caused to the surrounding tissue can be finely determined.

This makes it possible to sufficiently treat the tumor without producing any side effect due to an excessive focus intensity, thus allowing safe, efficient irradiation treatment.

(Second Embodiment)

Figure 4:
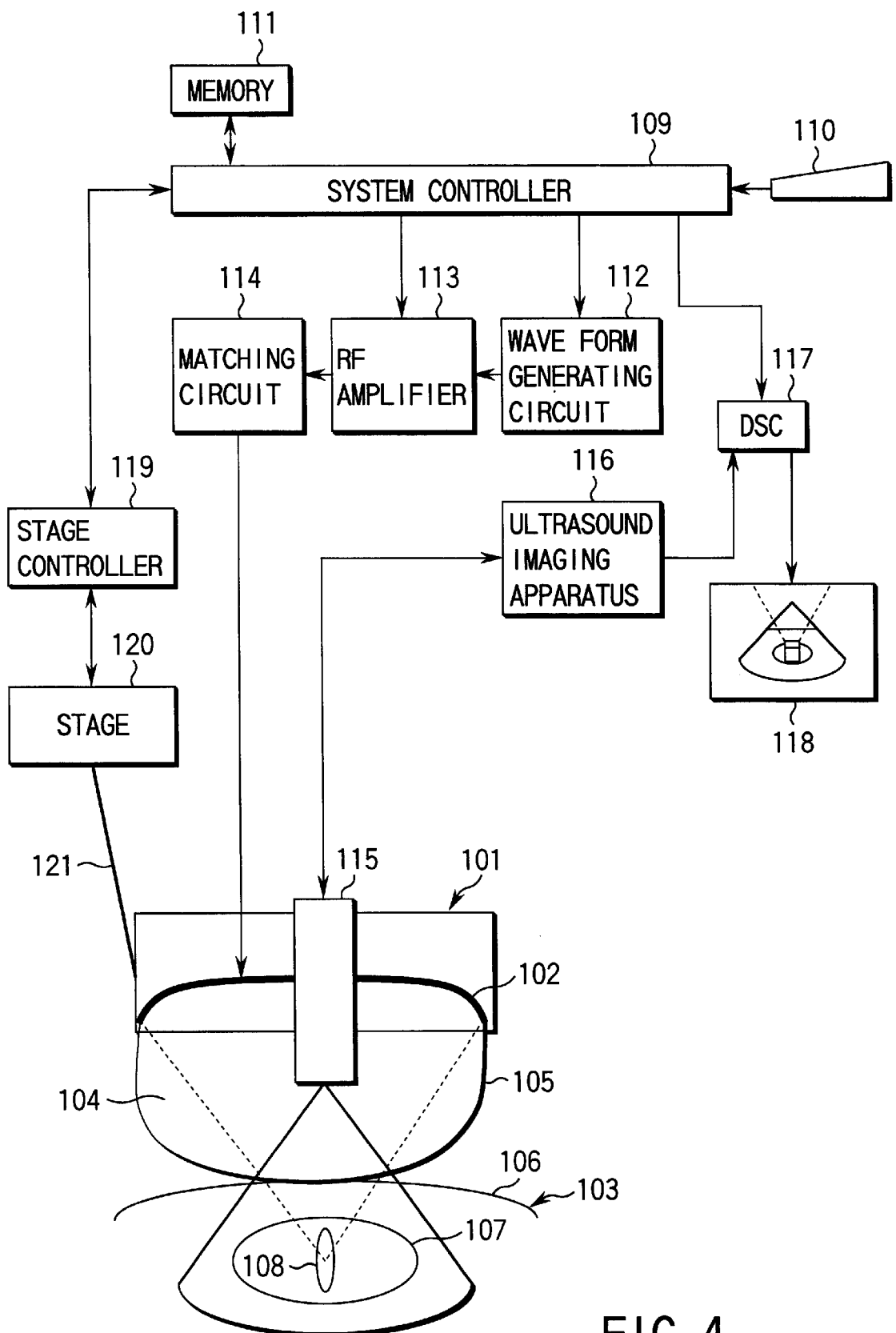
FIG. 4 is a block diagram showing the arrangement of an ultrasound treatment apparatus according to the second embodiment of the present invention.

As shown in FIG. 4, an applicator 101 is comprised of a treatment ultrasound source 102 which is made up of a plurality of piezoelectric elements and generates strong treatment ultrasound, coupling liquid 104 for guiding strong treatment ultrasound to a patient 103, coupling film 105, and imaging ultrasound probe 115 for acquiring a B-mode image inside the body.

In medical treatment, the patient 103 is instructed to lie on a bed and fixed at a predetermined position. The applicator 101 is placed on the body surface of the patient 103, and the coupling film 105 is brought into contact with a body surface 106 covered with an ultrasound jelly or the like. In positioning the applicator 101, a B-mode image including a tumor (tumor) 107 is reconstructed by an ultrasound imaging apparatus 116 on the basis of a reflected wave signal from the patient 103 which is acquired by the imaging ultrasound probe 115 inserted in the center of the applicator 101, and the position of an ultrasound focus 108 of the treatment ultrasound source 102 is displayed on a CRT 118 through a DSC 117 so as to be superimposed on the reconstructed image.

A command is output to a stage controller 119 in accordance with a signal from a system controller 109 to align the focal position on this image with the tumor (tumor) 107 inside the patient 103. The stage controller 119 then controls a stage 120 and arm 121 to move the applicator 101 in accordance with the instruction, thereby positioning the applicator 101.

Figure 5:
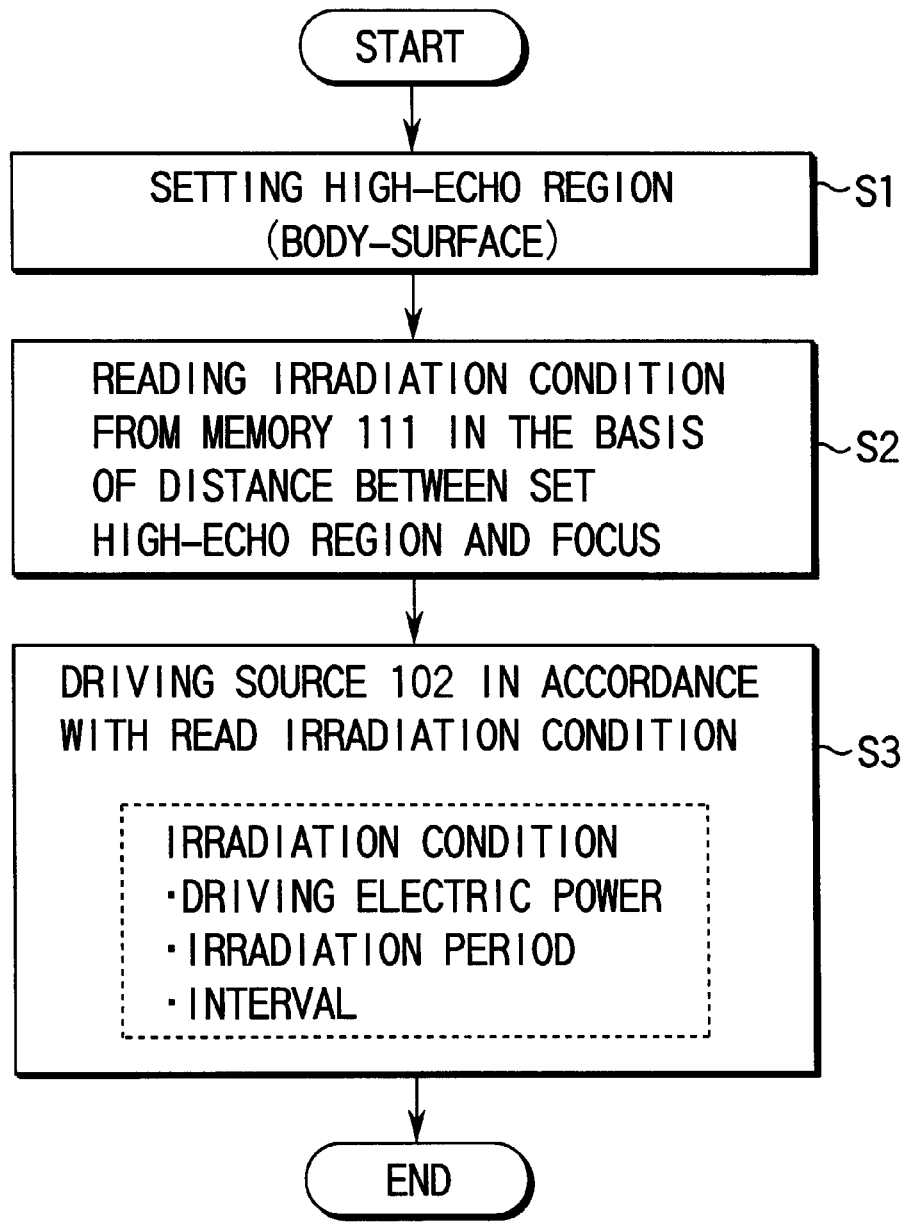
FIG. 5 is a flow chart roughly showing a procedure for setting an irradiation condition in the second embodiment.

In this embodiment, as shown in FIG. 5, after positioning is completed, the operator designates, on a console panel 110, a hyper Echoic region represented by the body surface of a patient which exhibits a large acoustic impedance difference (step S1). This hyper Echoic region is a region which noticeably generates heat upon irradiation of treatment ultrasound. This region includes the boundary between internal organs, the body surface of the patient, and the like. In this case, a case of a body surface as a hyper Echoic region will be described. In this embodiment, an irradiation condition (driving electric power, irradiation period, and irradiation interval) under which degeneration of a tumor is appropriately caused, and damage to the body surface (hyper Echoic region) is minimized is read out from a memory 111 (step S2). In accordance with a command from the system controller 109, movement/irradiation control on the applicator 101 is performed (step S3).

In this irradiation operation, a wave form generating circuit 112 generates a wave form signal in accordance with the irradiation condition stored in the memory 111. This wave form signal is amplified by an RF amplifier 113 to excite the piezoelectric elements of the treatment ultrasound source 102 through a matching circuit 114.

In this embodiment, the operator may manually designate a hyper Echoic region between the treatment ultrasound source 102 and the focus by using the console panel 110, or a region in which the intensity of a B-mode image exceeds a threshold may be automatically extracted as a hyper Echoic region. In addition, since the probe 115 is brought into contact with the body surface, the distance from the treatment ultrasound source 102 to the body surface may be calculated on the basis of the protrusion amount of the probe 115 from the treatment ultrasound source 102. Alternatively, an irradiation condition may be set as a default by designation of a treatment depth or automatic detection alone on the basis of the general anatomical position relationship between the applicator and the contact position.

Figure 6A:
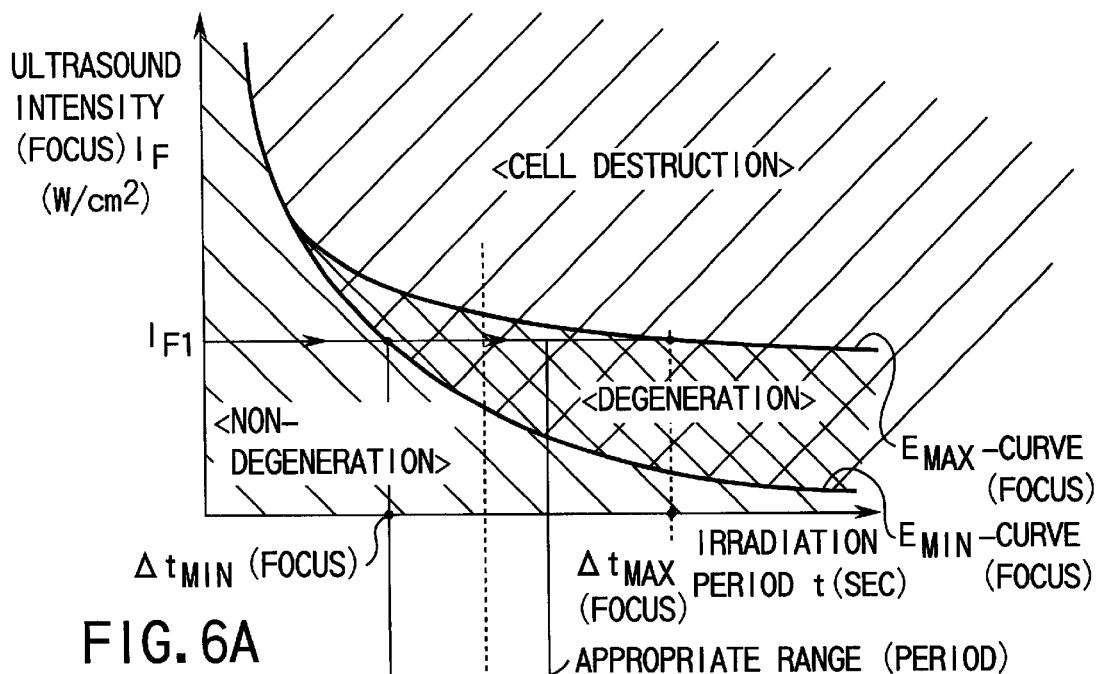
FIG. 6A is a graph showing the relationship between the state of a cell and the ultrasound intensity and irradiation time at a focus.
Figure 6B:
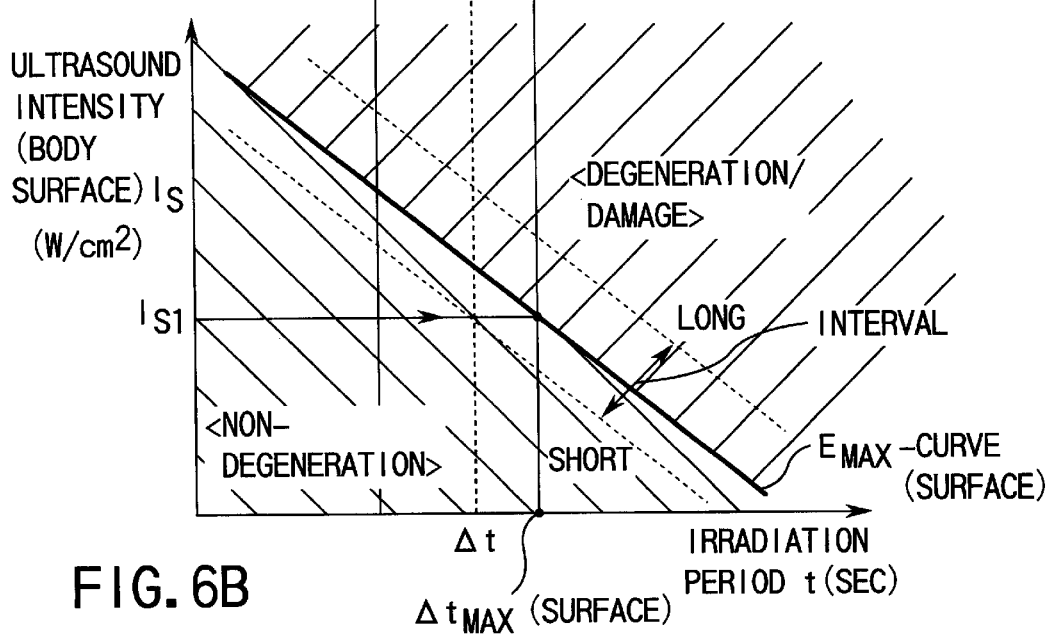
FIG. 6B is a graph showing the relationship between the state of a cell and the ultrasound intensity and irradiation time on the body surface of a patient.

FIGS. 6A and 6B are characteristic graphs based on which an appropriate irradiation condition is set. FIG. 6A shows the appropriate range of optimization indexes associated with a focus. FIG. 6B shows the appropriate range of optimization indexes associated with a body surface. In this embodiment, to determine an irradiation condition (driving electric power and irradiation period), a focus intensity and irradiation period are determined by using optimization indexes, and the focus intensity is converted into a driving electric power on the basis of an ultrasound attenuation coefficient and the like.

Figure 7:
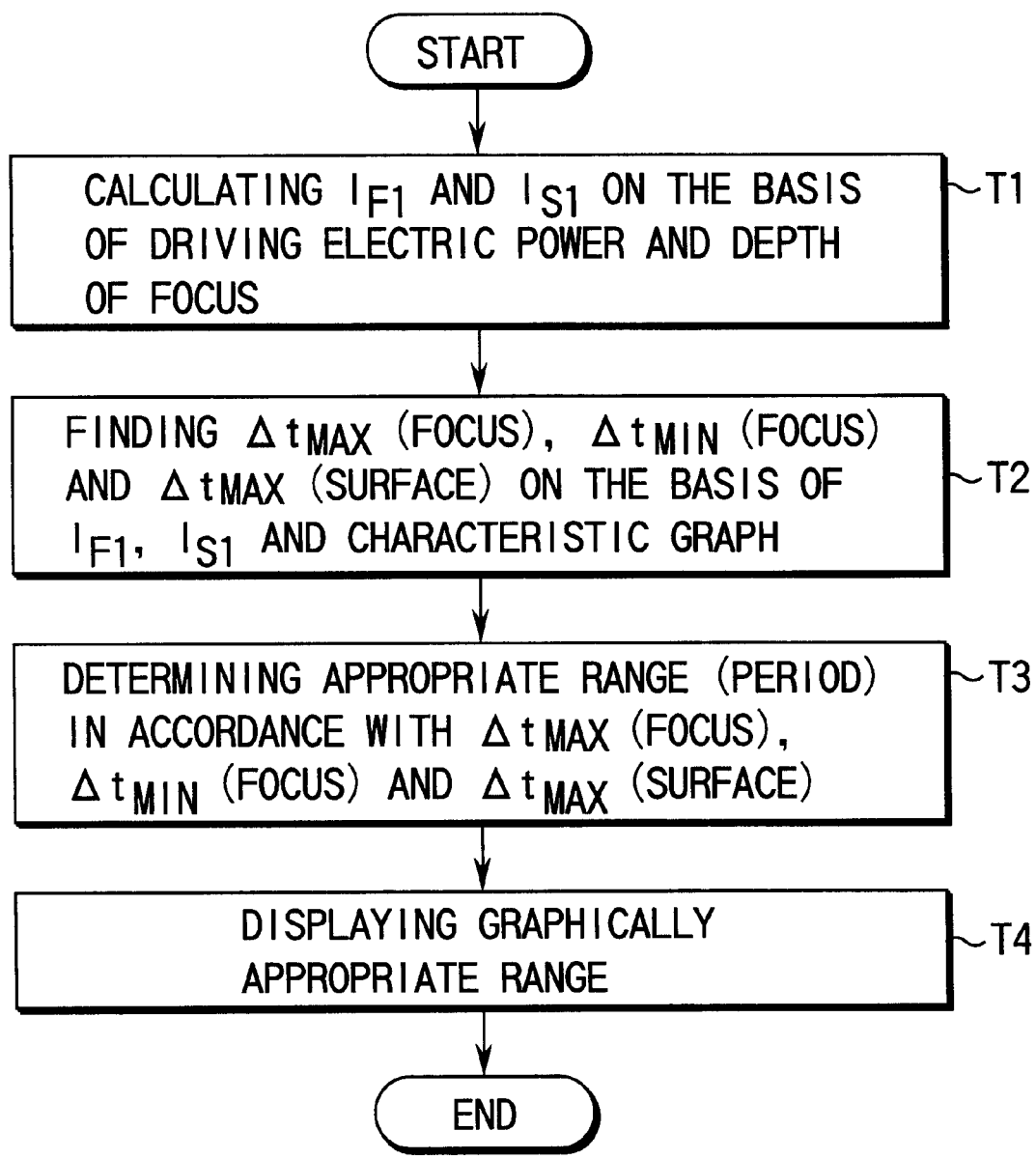
FIG. 7 is a flow chart showing the details of a procedure for setting an irradiation condition in the second embodiment.

Irradiation condition setting operation will be described in detail below with reference to FIGS. 6A, 6B, and 7. Referring to FIG. 6A, $E_{MAX}$-CURVE (FOCUS) indicates the upper limit value of optimization indexes; and $E_{MIN}$-CURVE (FOCUS), the lower limit value of the optimization indexes. That is, no cell destruction occurs in a tumor and appropriate degeneration occurs as long as the optimization index falls within the range of $E_{MAX}$-CURVE (FOCUS) to $E_{MIN}$-CURVE (FOCUS). Referring to FIG. 6B, $E_{MAX}$-CURVE (SURFACE) indicates the upper limit value of the optimization indexes within which the body surface is not damaged.

First of all, the operator sets a driving electric power and irradiation period. When, for example, a driving electric power is set by the operator, the system controller 109 calculates an ultrasound intensity (focus intensity) $I_{F1}$ at the focus corresponding to the driving electric power and ultrasound intensity (body surface intensity) $I_{S1}$ on the basis of the distance between the tumor (focus) 107 and the body surface (hyper Echoic region) and an attenuation coefficient (step T1).

The system controller 109 refers to the characteristic graph of FIG. 6A on the basis of the focus intensity $I_{F1}$. With this operation, an upper limit $\Delta t_{MAX(FOCUS)}$ of an irradiation period within which no cell destruction occurs in a tumor and a lower limit $\Delta t_{MIN(FOCUS)}$ of an irradiation period within which non-degeneration of the tumor does not occur are specified (step T2). In addition, the system controller 109 refers to the characteristic graph of FIG. 6B on the basis of the body surface intensity $I_{S1}$. With this operation, an upper limit $\Delta t_{MAX(SURFACE)}$ of an irradiation period within which the body surface is not damaged is specified (step T2).

An appropriate irradiation period range in which the tumor appropriately degenerates and the body surface is not damaged is determined within the range of $\Delta t_{MIN(FOCUS)}$ to $\Delta t_{MAX(SURFACE)}$ from $\Delta t_{MAX(FOCUS)}$, $\Delta t_{MIN(FOCUS)}$, and $\Delta t_{MAX(SURFACE)}$ (step T3).

Figure 8A:
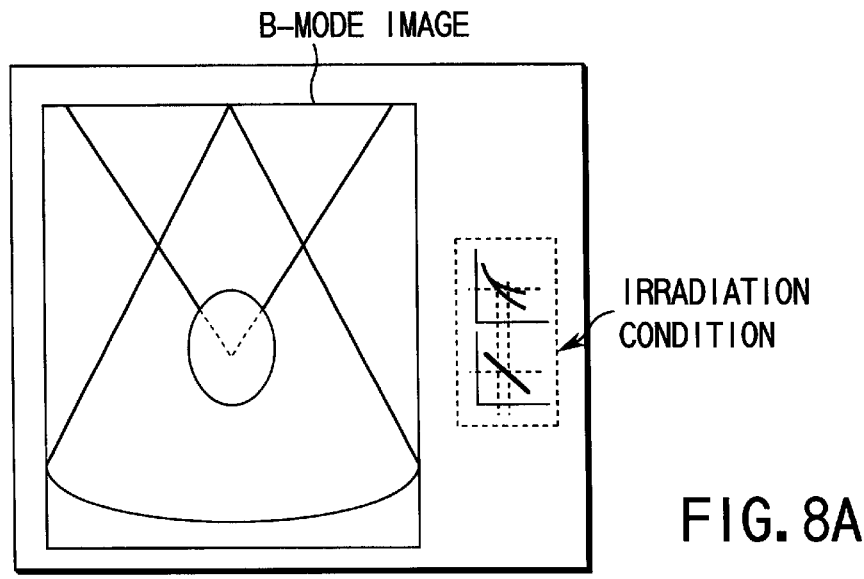
FIG. 8A is a view showing an example of display of an irradiation condition in the second embodiment.
Figure 8B:
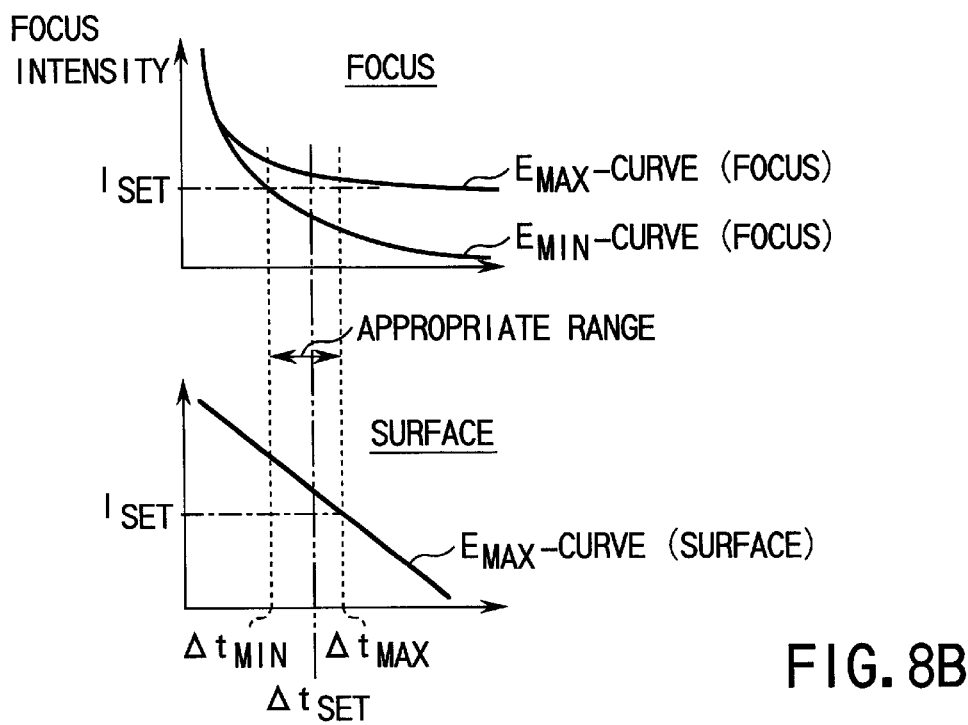
FIG. 8B is a graph showing the details of the display of the irradiation condition in FIG. 8A.

When the appropriate irradiation period range is determined in this manner, a characteristic curve associated with the focus and a characteristic curve associated with the body surface are linked to each other and graphically displayed, as shown in FIGS. 8A and 8B (step T4). Finally, the operator sets an irradiation period $\Delta_{tset}$ within this appropriate range.

Figure 8C:
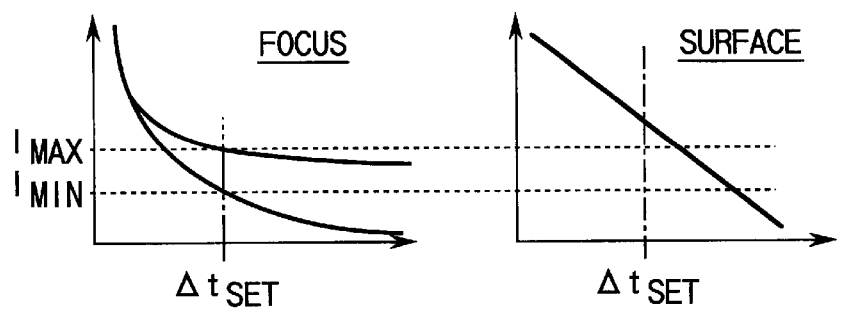
FIG. 8C is a graph showing the details of another example of the display of the irradiation condition in FIG. 8A.

According to the above description, a driving electric power is set first, and then an appropriate irradiation period range corresponding to the driving electric power is obtained. However, an irradiation period may be set first, and then an appropriate focus intensity range corresponding to the irradiation period may be obtained. The procedure for obtaining this appropriate driving electric power range is the same as that for obtaining an appropriate irradiation period range. In this case, as shown in FIG. 8C, a characteristic curve associated with the focus and a characteristic curve associated with the body surface are linked to each other and graphically displayed, and hence the operator sets a focus intensity within this appropriate range.

Although any value may be set in irradiation setting, an upper limit value is used to ensure the maximum degeneration amount at one point. If this setting plan is determined in advance, a driving electric power and irradiation period can be automatically determined. The wave form generating circuit 112 is driven on the basis of this determination to generate strong ultrasound from the applicator 101.

In practice, irradiation of ultrasound is often intermittently repeated. Since the temperature of the body surface decreases in irradiation intervals, the appropriate index associated with the body surface varies depending on the length of this interval (FIG. 6B).

The correlation between $I_{F1}$ and $I_{S1}$ can be obtained by giving to a predetermined function parameters such as the focusing degree and resonance frequency of the treatment ultrasound source 102, the distance between the focus and the body surface, and attenuation. This function is stored in the memory 111 in advance, and the system controller 109 calculates the correlation on the basis of the parameters.

Figure 9:
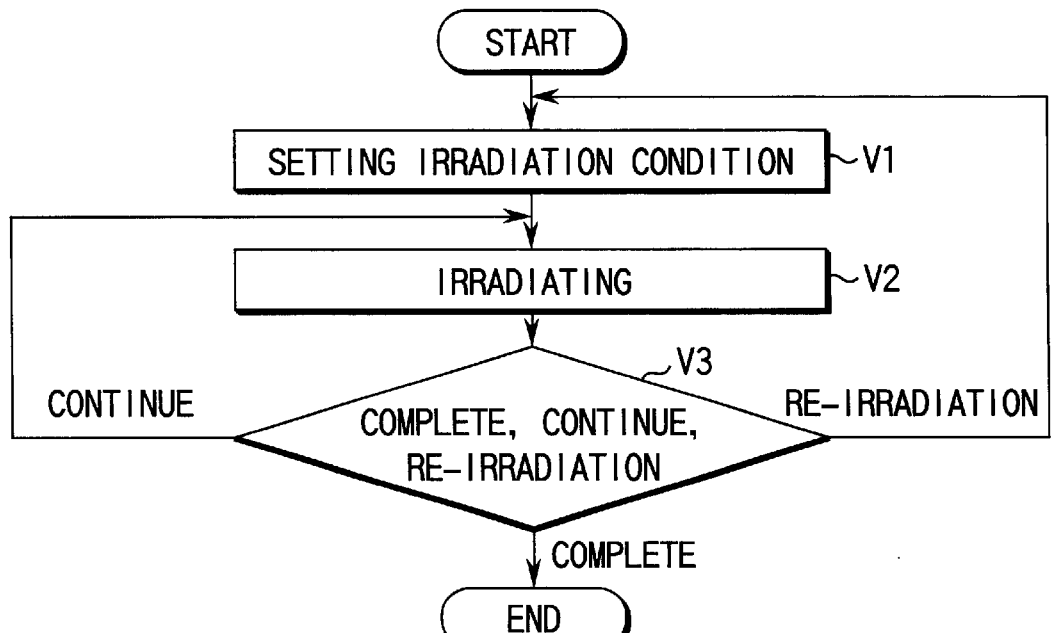
FIG. 9 is a flow chart showing a procedure for completing irradiation in the second embodiment.

An appropriate range of focus intensities or irradiation periods is obtained in the above manner (step V1 in FIG. 9). Treatment ultrasound is then generated under an irradiation condition set within this range to execute medical treatment (step V2). Thereafter, the operator checks the state of the tumor, and completes or re-executes the medical treatment or re-sets an irradiation condition, as needed (step V3).

According to the above description, an appropriate range of focus intensities or irradiation periods is obtained according to optimization indexes. However, this appropriate range may be calculated in advance and stored in the memory 111.

Figure 10:
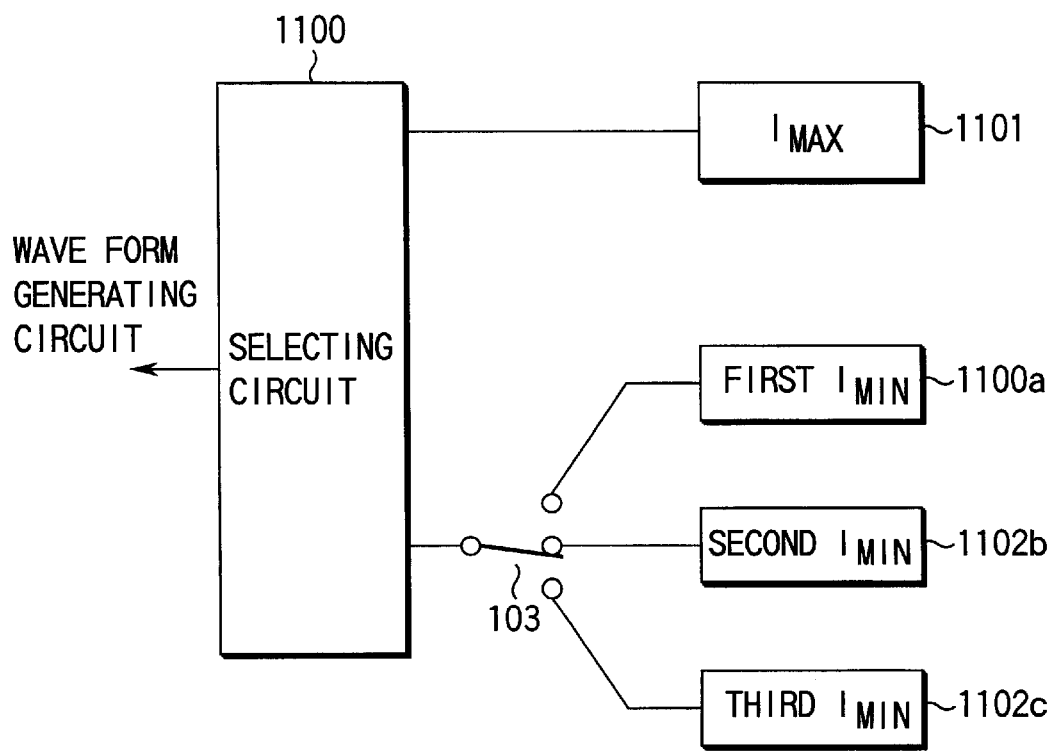
FIG. 10 is a block diagram showing the arrangement of an appropriate range setting circuit for ultrasound intensities in the second embodiment.

In addition, an appropriate range is defined by one upper limit value and one lower limit value. As shown in FIG. 10, however, an upper limit value/lower limit value selecting circuit 1100 may be connected to the system controller 109 to selectively use one upper limit value 1101 and a plurality of lower limit values 1102a, 1102b, and 1102c through a switch 103.

(Third Embodiment)

Figure 11:
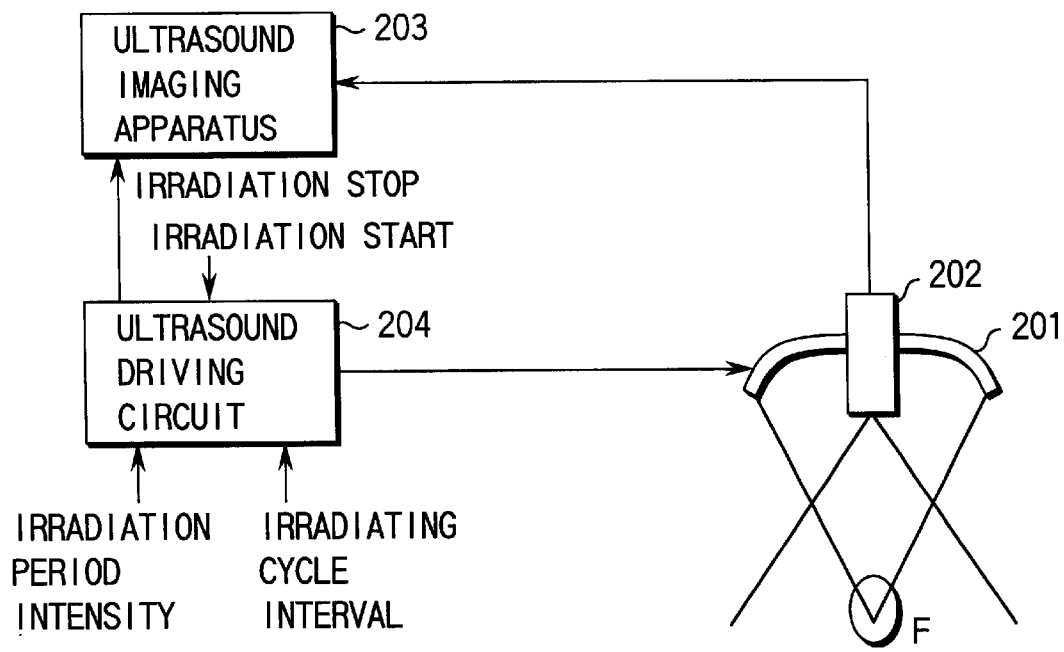
FIG. 11 is a block diagram showing the arrangement of an ultrasound treatment apparatus according to the third embodiment of the present invention.

FIG. 11 shows the arrangement of an ultrasound treatment apparatus according to the third embodiment of the present invention. An ultrasound source 201 is made of a piezoelectric element having a concave surface and serving to irradiate a tumor with treatment ultrasound. The treatment ultrasound is brought to a focus F determined by the curvature of the concave surface.

An imaging ultrasound probe 202 is placed in the center of the ultrasound source 201. An ultrasound imaging apparatus 203 performs signal processing for the ultrasound signal transmitted/received by the ultrasound probe 202. The B-mode image obtained by this signal processing is displayed.

The operator always monitors the state of the tumor while visually checking the tumor with the B-mode image. When ultrasound treatment is to be started in this environment, the operator inputs an irradiation condition to an ultrasound driving circuit 204 through an operation panel (not shown) of the ultrasound treatment apparatus. In this operation, the operator inputs the irradiation period and intensity of treatment ultrasound, irradiation stop cycle, irradiation stop period, and the like in accordance with a treatment plan upon preliminary diagnosis based on the information obtained by the B-mode image and other diagnosis means. Thereafter, irradiation of ultrasound is started.

In determining the irradiation condition for the ultrasound treatment apparatus, an irradiation cycle and period are determined first by an irradiation stop period setting means for determining an observation condition during irradiation. More specifically, for an internal organ that does not easily move, a relatively long irradiation cycle and relatively long stop interval can be set. Ultrasound may be continuously irradiated without setting any stop period depending on the target portion. In contrast to this, for an internal organ that moves, a short irradiation period and short stop period can be set. Obviously, a fixed cycle and period may be set.

Figure 12:
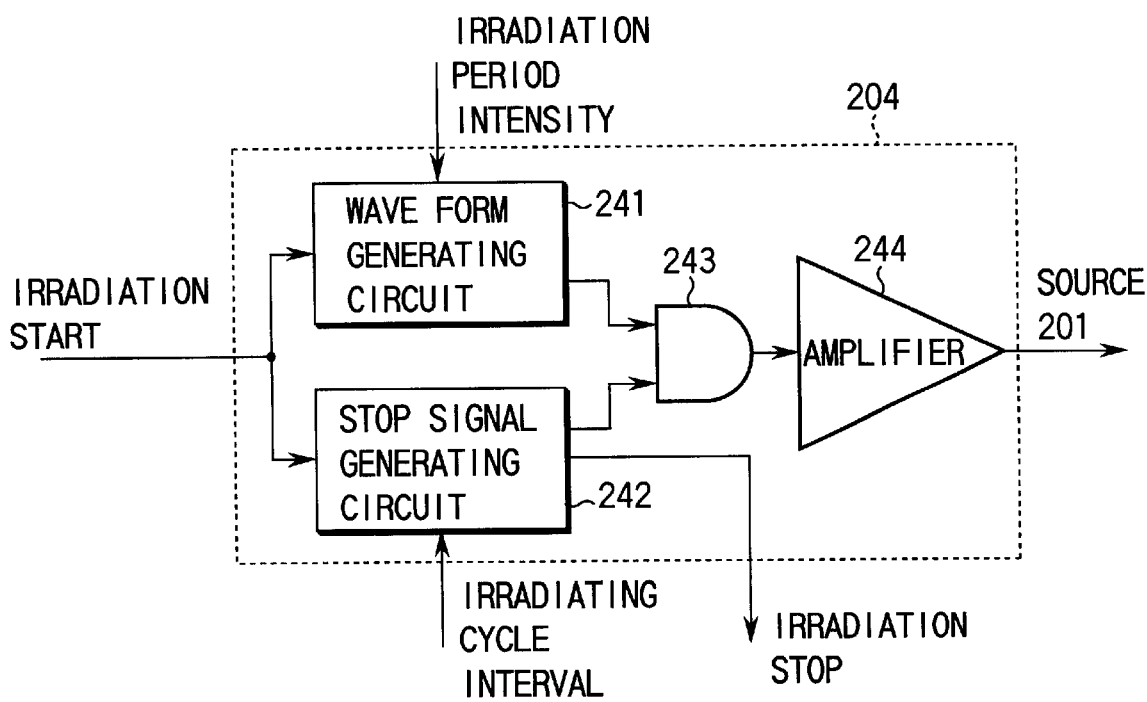
FIG. 12 is a block diagram showing the arrangement of an ultrasound driving circuit 204 in FIG. 11.

FIG. 12 shows the arrangement of the ultrasound driving circuit 204 in FIG. 11. A wave form generating circuit 241 generates an initial driving signal in accordance with the irradiation condition set. A stop signal generating circuit 242 generates stop signals corresponding to an irradiation period, cycle, and stop period of treatment ultrasound. A signal synthesizer 243 generates a driving signal by synthesizing the initial driving signal with a stop signal. This driving signal is amplified by an amplifier 244 with an amplification factor corresponding to the irradiation condition. With this operation, a driving signal for driving the piezoelectric element of the ultrasound source 201 is generated.

(Dual Mode)

Figure 13:
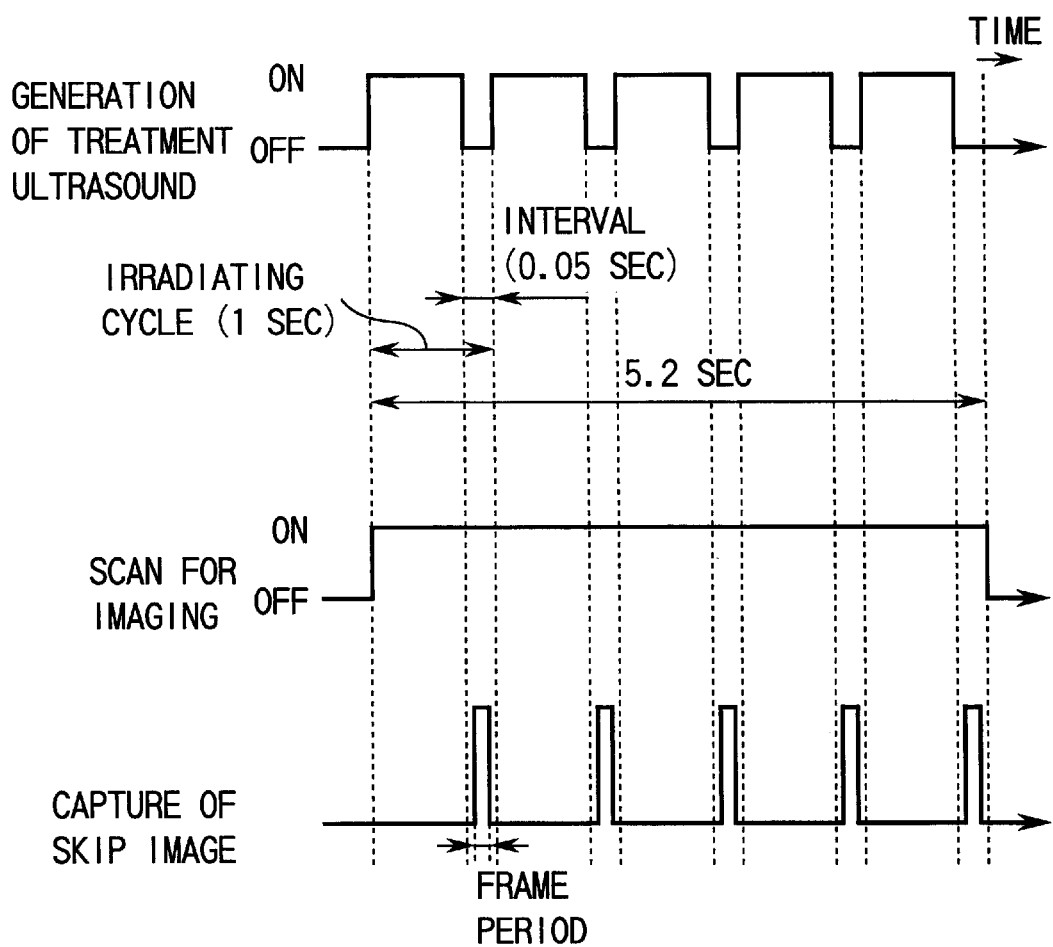
FIG. 13 is a timing chart showing scanning operation and still image capturing operation corresponding to generation of treatment ultrasound in the dual mode in the third embodiment.

FIG. 13 shows the operation in a dual mode in the third embodiment. Treatment ultrasound is intermittently generated in an arbitrary irradiation cycle. An irradiation period, irradiation interval (stop period), and irradiation cycle can be arbitrarily set by the operator. For example, the irradiation period, irradiation interval (stop period), irradiation cycle, and treatment period are respectively set to 0.95 sec, 0.05 sec, 1 sec, and 5.2 sec.

While such treatment ultrasound is intermittently generated, scanning of a cross-section inside the patient is continuously repeated with imaging ultrasound. The time required for one complete scan on this cross-section, i.e., the frame period, is set to be shorter than the irradiation interval (stop period), 0.05 sec. In contrast to this, the above irradiation interval (stop period) is set to be longer than the frame period.

B-mode image is continuously generated by continuously repeated scanning. When scanning is performed while treatment ultrasound is generated, a B-mode image with an excessively high intensity is obtained owing to high echo of treatment ultrasound. When scanning is performed while treatment step S is stopped, no high echo of treatment ultrasound is present. Therefore, a B-mode image with an appropriate intensity can be obtained.

Figure 14:
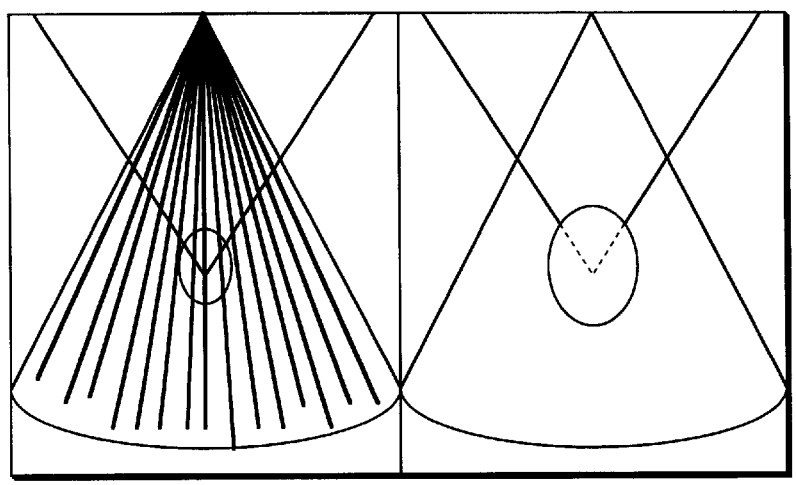
FIG. 14 is a view showing a dual display window corresponding to the operation in FIG. 13.

As shown in FIG. 14, continuously generated B-mode image data is played as a moving image on the monitor in real time. In the ultrasound imaging apparatus 203, B-mode image data corresponding to scanning performed during a stop period of treatment ultrasound is picked up from the continuously generated B-mode image data in synchronism with stopping operation of the treatment ultrasound, and is displayed beside the moving image. This picked-up B-mode image is switched in the irradiation cycle (1 sec). This B-mode image is therefore displayed as an image (referred to as a skip image) at 1 frame per sec, which is neither a moving image nor a still image.

As described above, a B-mode image obtained during a stop period of treatment ultrasound has an appropriate intensity, and hence allows the operator to observe the tissue form. In contrast to this, a B-mode image obtained during generation of treatment ultrasound has an excessively high intensity, and hence looks completely white. This makes it impossible to see the tissue form. That the B-mode image looks completely white indicates that the corresponding portion is actually irradiated with treatment ultrasound. The operator can therefore check the progress of treatment, any focus deviation from the tumor, and the like with a skip image while checking irradiation of treatment ultrasound with a moving image.

(Single Mode)

Figure 16:
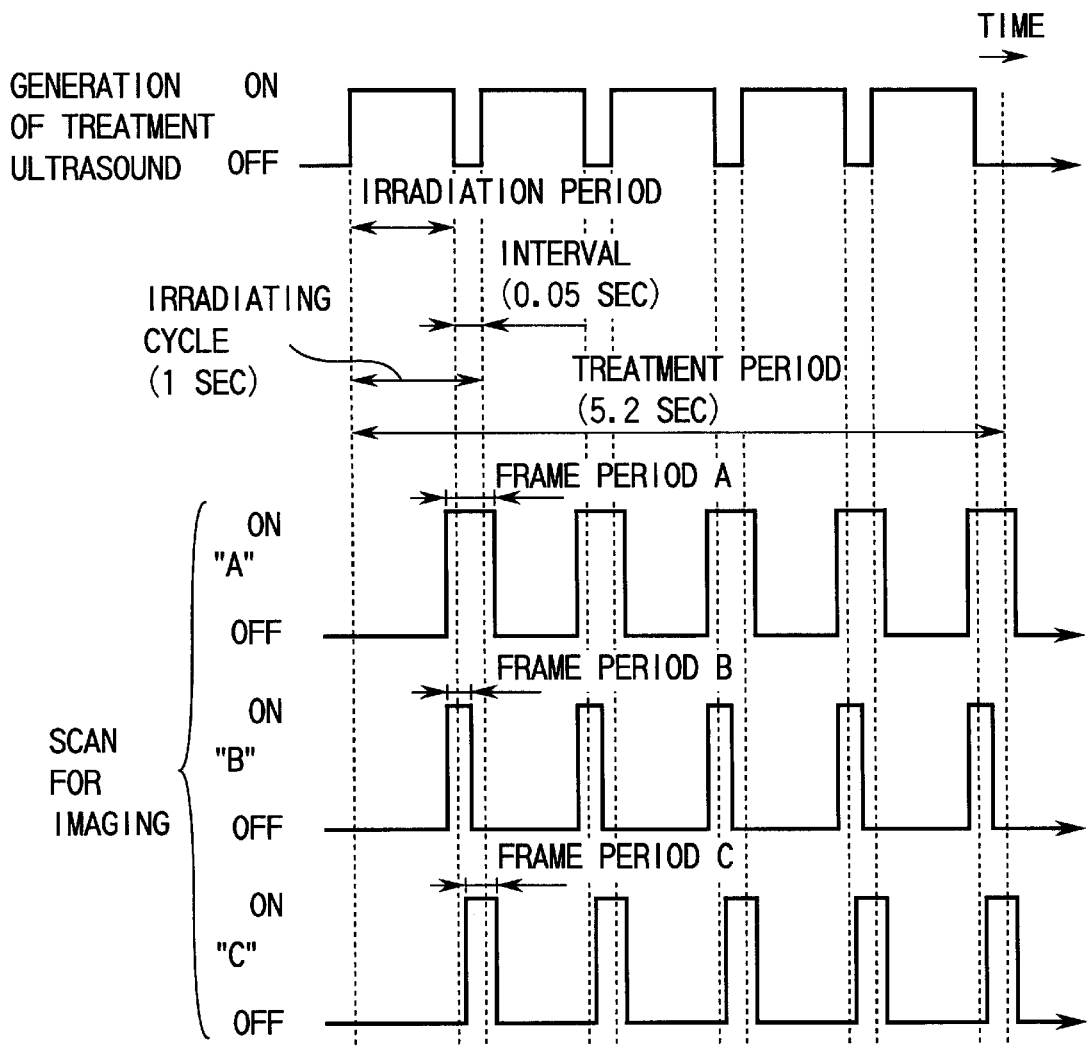
FIG. 16 is a timing chart showing scanning operation corresponding to generation of treatment ultrasound in the single mode in the third embodiment.

FIG. 16 shows the operation in a single mode in the third embodiment. In the single mode, only one image is displayed, but this one image allows the operator to observe a tissue form and check irradiation of treatment ultrasound as in the dual mode. Treatment ultrasound is intermittently generated in an irradiation cycle. While such treatment ultrasound is intermittently generated, a cross-section inside a patient is scanned with imaging ultrasound such that some of scan periods, e.g., the first half portion of a scan period (type B), the second half portion of a scan period (type C), and the first and second half portions of a scan period excluding a central portion (type A) overlap a generation period of treatment ultrasound in synchronism with a stop period of treatment ultrasound.

In this mode as well, an irradiation period, irradiation interval (stop period), and irradiation cycle can be arbitrarily set by the operator. According to type A, the frame period required for one complete scan on a cross-section must be longer than a stop period of treatment ultrasound. In types B and C, such a restriction is not imposed and hence frame periods can be arbitrarily set.

Figure 17A:
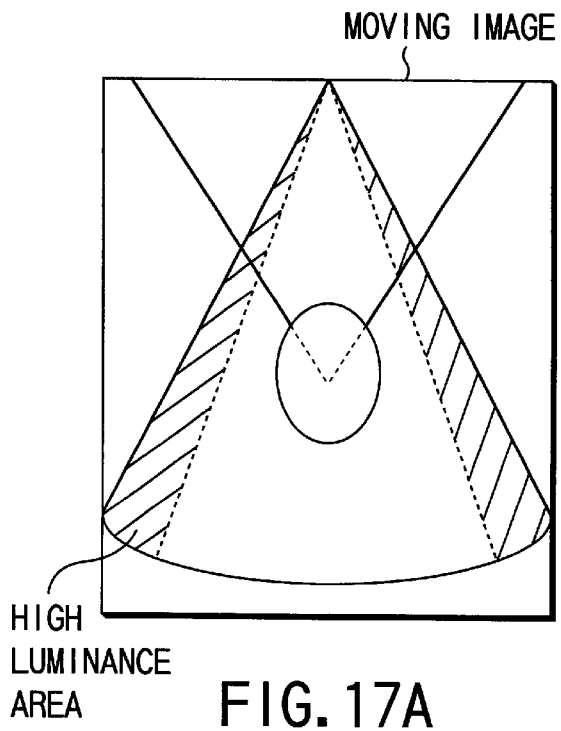
FIG. 17A is a view showing a single display window corresponding to operation "A" in FIG. 16.
Figure 17B:
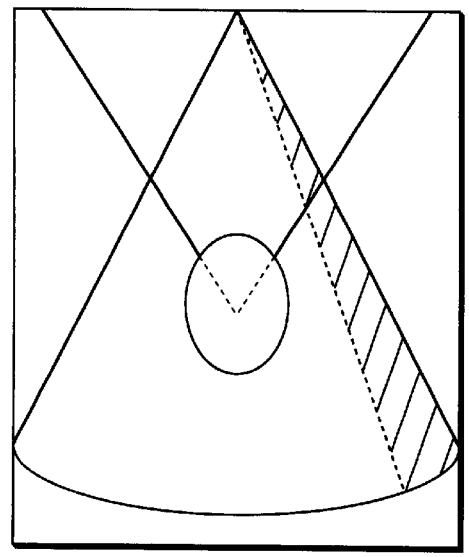
FIG. 17B is a view showing a single display window corresponding to operation "B" in FIG. 16.
Figure 17C:
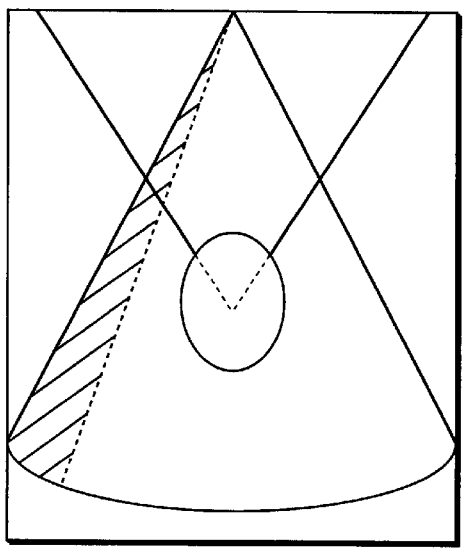
FIG. 17C is a view showing a single display window corresponding to operation "C" in FIG. 16.

The B-mode image obtained by this intermittent scanning is displayed as a skip image. Since some of frame periods overlap a generation period of treatment ultrasound, these portions of the B-mode image which correspond to generation periods of treatment ultrasound look completely white, and those portions of the B-mode image which correspond to stop periods of treatment ultrasound are displayed as B-mode forms, as shown in FIGS. 17A, 17B, and 17C. The operator can therefore check the progress of treatment, any focus deviation from the tumor, and the like with the skip image, while checking irradiation of treatment ultrasound with the moving image.

Figure 18:
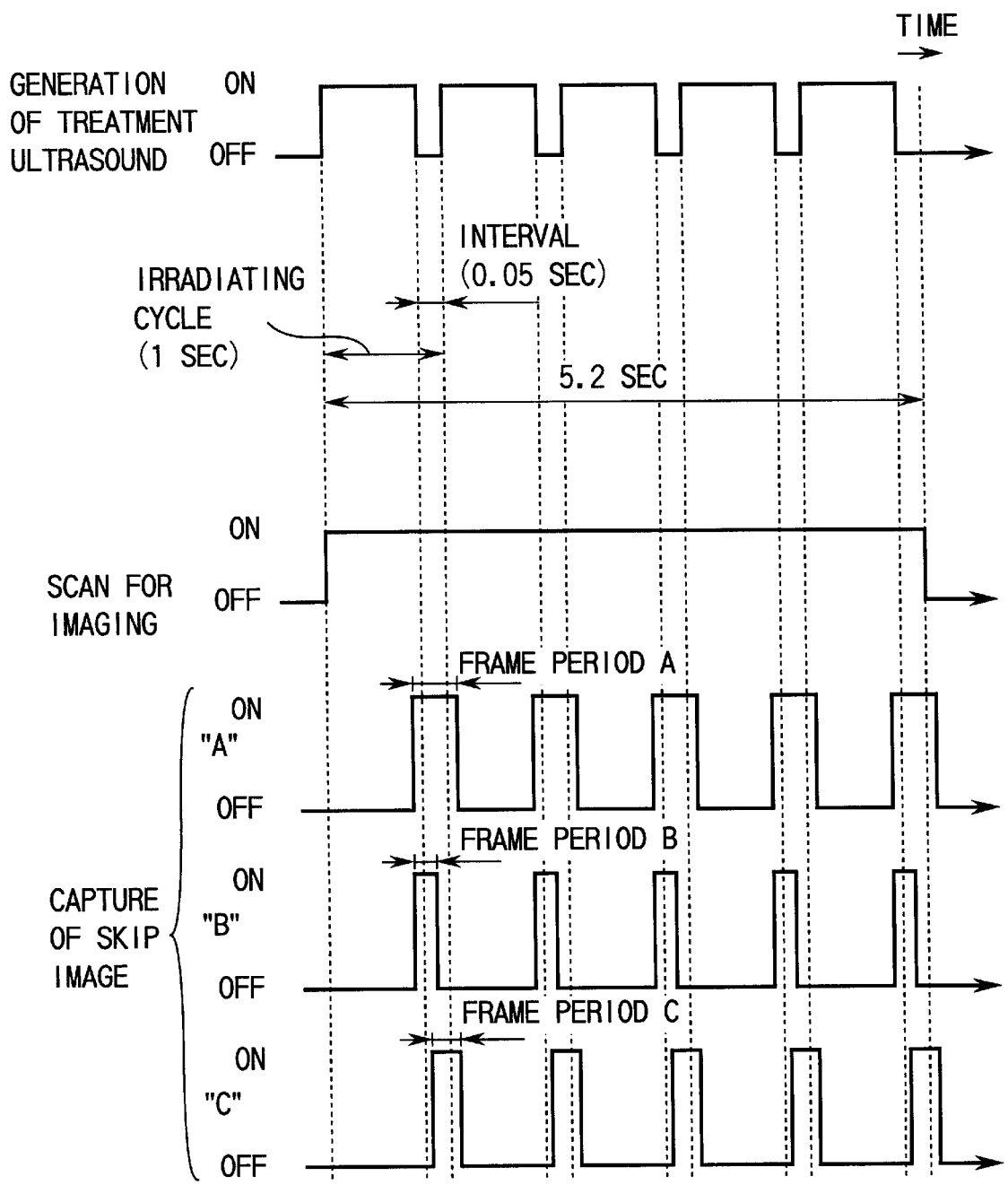
FIG. 18 is a timing chart showing another scanning operation corresponding to generation of treatment ultrasound in the signal mode in the third embodiment.

In the single mode, the operator may continuously repeat scanning, as shown in FIG. 18, instead of intermittently performing scanning in synchronism with stop periods of treatment ultrasound, so as to pick up B-mode images in synchronism with stop periods of treatment ultrasound and display only picked-up B-mode images as skip images.

Figure 15:
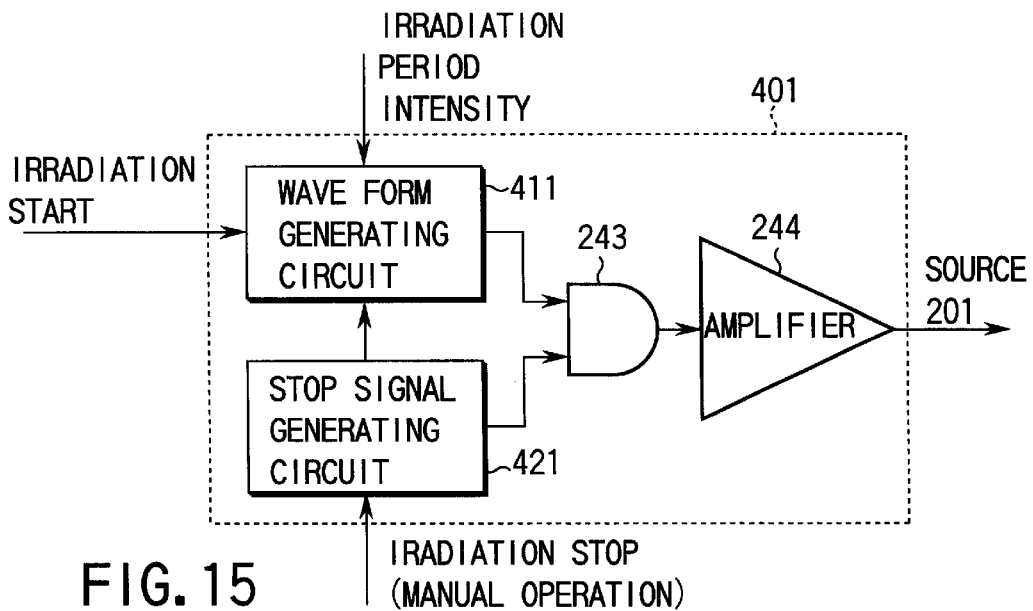
FIG. 15 is a block diagram showing another example of the arrangement of the ultrasound driving circuit 204 in FIG. 11.

Treatment ultrasound may be cyclically stopped or may be arbitrarily stopped at arbitrary time points for arbitrary periods in accordance with the manual operation performed by the operator, as shown in FIG. 15. During stopping operation, therefore, irradiation of treatment ultrasound is stopped, and a B-mode image showing a tissue form is displayed. If, for example, the target internal organ does not move much, the operator need not frequently stop treatment ultrasound to frequently check for any focus deviation from a tumor. In contrast to this, if the target internal organ moves greatly, the operator must frequently stop treatment ultrasound to frequently check for any focus deviation from the tumor. The manual operation can flexibly cope with such states.

When treatment ultrasound is manually stopped, the stop period may become too long to make a tumor appropriately degenerate in the treatment period. In order to prevent this, a wave form generating circuit 411 prolongs the treatment period by a period during which a stop signal generating circuit 421 generates a stop signal.

Figure 19:
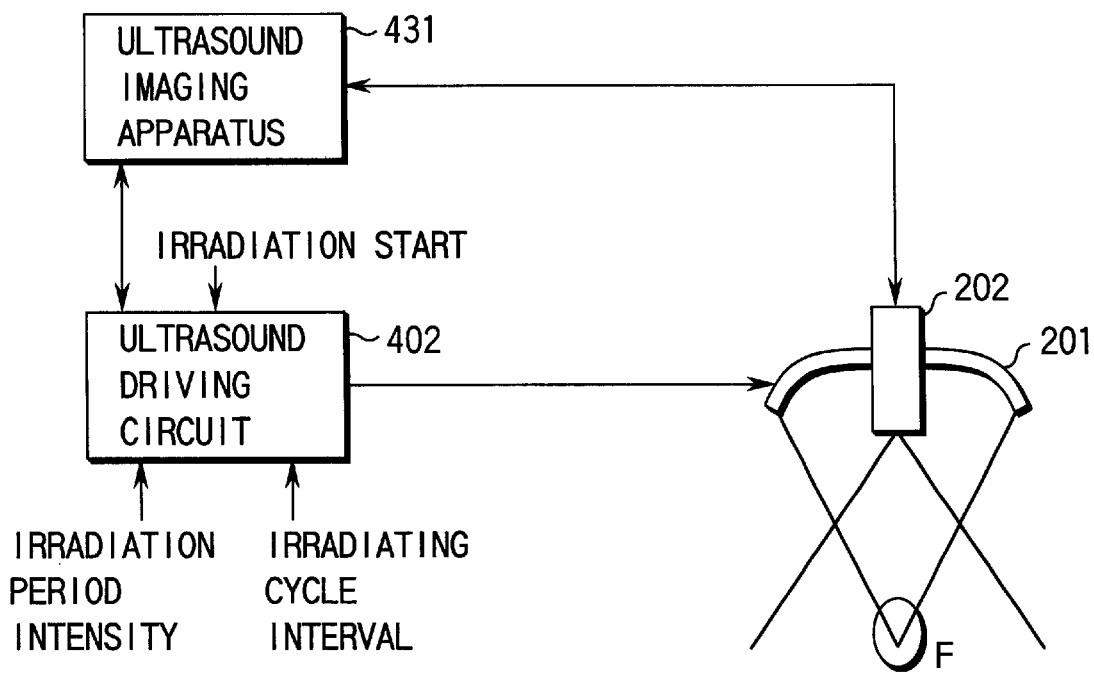
FIG. 19 is a block diagram showing a modification of the third embodiment.
Figures 20A, 20B:
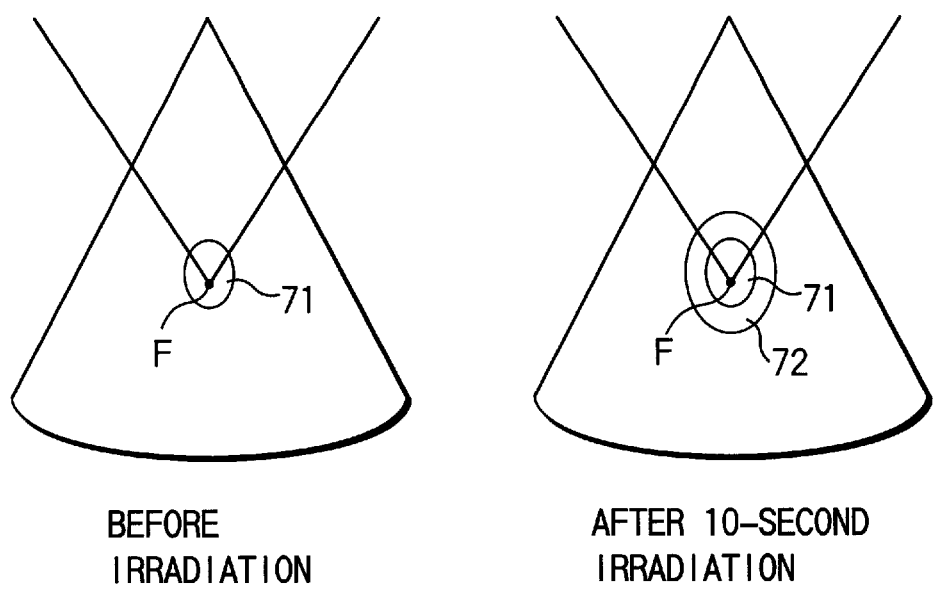
FIG. 20A is a view showing the state of a tumor before irradiation of treatment ultrasound in the third embodiment.
FIG. 20B is a view showing the state of the tumor after irradiation of treatment ultrasound.

FIG. 19 shows an ultrasound treatment apparatus having the function of supporting a check on the progress of treatment. FIG. 20A shows the state of a tumor before treatment. FIG. 20B shows the state of the tumor after treatment. An ultrasound imaging apparatus 431 extracts the intensity of a region 71 including the focus F from a B-mode image corresponding to a stop period of treatment ultrasound. In general, the echo gradually increases in intensity to increase the intensity. For example, the intensity of a region 72 in FIG. 20B increases 10 sec after the start of treatment.

When the maximum value, total value, or average value of intensities in this region 72 reaches a predetermined threshold, it is determined that the tumor has appropriately degenerated, and the ultrasound imaging apparatus 431 transmits a driving stop signal to an ultrasound driving circuit 402. In accordance with this signal, treatment is completed. This can prevent destruction of morbid tissue.

Although intensity information is checked on the basis of the progress of treatment, this check may be made by analyzing the frequency component of an echo and using an index representing the rate of change in this frequency component. Similar control can be performed by using changes in echo intensity from a focus region or frequency characteristics instead of using a B-mode image. In this case, the ultrasound source 201 is used for reception as well as transmission, and weak ultrasound pulses are transmitted from the ultrasound source 201 during irradiation stop periods. Alternatively, a tumor is irradiated with weak ultrasound from the ultrasound source 201, and echoes from the tumor are received by the ultrasound probe 202. The received signals are analyzed to generate information that allows the operator to check the progress of treatment.

If the tumor is larger than the focus, the focus F must be moved intermittently or continuously, and treatment ultrasound must be repeatedly irradiated in synchronism with the movement of the focus F. In executing this treatment method, the irradiation condition (intensity and irradiation period) for treatment ultrasound must be set carefully to appropriately cause degeneration of a tumor and prevent degeneration of normal tissue around the tumor. In this embodiment, the irradiation condition can be optimized. When the focus F is to be continuously irradiated with treatment ultrasound, in particular, the index must be changed in consideration of the overall frequency/energy density.

As described above, according to this embodiment, the operator can appropriately proceed with treatment while checking the progress of treatment and generation of treatment ultrasound.

Figure 21:
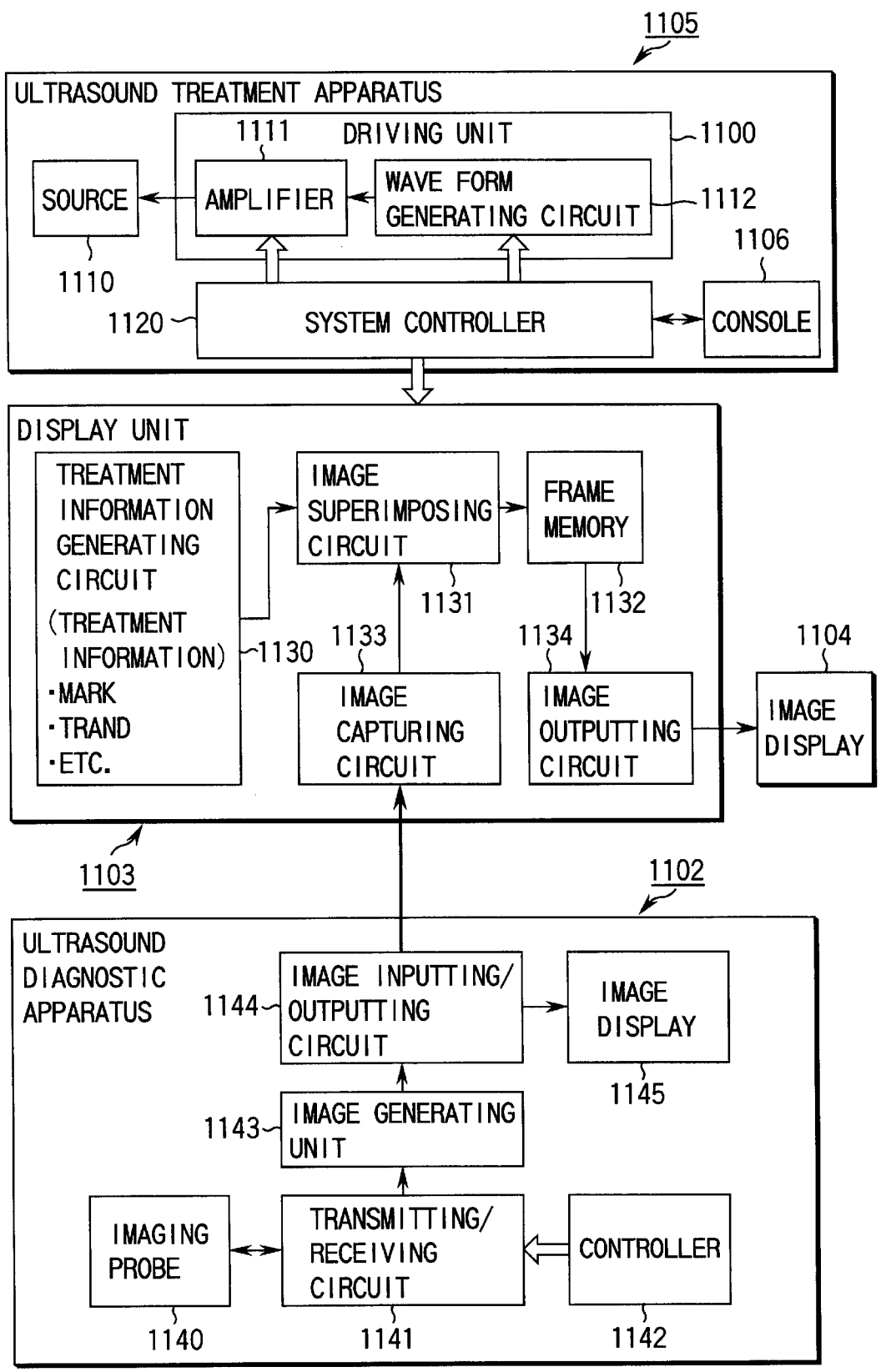
FIG. 21 is a block diagram showing the arrangement of an ultrasound treatment apparatus according to the fourth embodiment to which an ultrasound imaging function is externally added.

In the plurality of embodiments described above, an ultrasound treatment apparatus 1105 may have only a treatment function and image display function, while an external ultrasound diagnostic apparatus 1102 may have an image generating function, as shown in FIG. 21. When a tumor of a patient is to be irradiated with treatment ultrasound, the focus is set on the tumor before irradiation of treatment ultrasound. In adjusting the focus, the focal position is specified by the B-mode image obtained by the ultrasound diagnostic apparatus 1102.

After the focus adjustment, treatment ultrasound is irradiated from an treatment ultrasound source 1110 of the ultrasound treatment apparatus 1105. At this time, an amplifier 1111 amplifies the wave form signal generated by a wave form generating circuit 1112 to voltage-drive the treatment ultrasound source 1110, thereby irradiating treatment ultrasound from the treatment ultrasound source 1110.

The amplification type is properly selected for the amplifier 1111 according to a design intention in accordance with the wave form of a driving signal for driving the treatment ultrasound source 1110. For example, a general class B amplification circuit may be used. If the signal to be handled is a high-frequency pulse, an amplification unit of a switching type using a class D amplification circuit may be used to handle a large-output pulse signal.

A system controller 1120 controls the irradiation timing, wave form, amplification factor, irradiation count, and the like of the wave form generating circuit 1112 and amplifier 1111.

The system controller 1120 also controls the display contents generated by a display unit 1103 and its display timing. The display unit 1103 causes an image superimposing circuit 1131 to superimpose information necessary for treatment (to be referred to as treatment information hereinafter) on the B-mode image captured by an image capturing circuit 1133, and displays the superimposed image on an image display 1104 through a frame memory 1132 and image outputting circuit 1134.

The display unit 1103 is controlled by the system controller 1120 in accordance with the input state of a console 1106 and the overall state of the system. The ultrasound diagnostic apparatus 1102 has at least the same arrangement as that of a general ultrasound diagnostic apparatus. An imaging probe 1140 is driven by a transmitting/receiving circuit 1141.

The captured image is subjected to necessary image reconstruction processing in an image generating unit 1143. The resultant image is then displayed on an image display 1145 such as an image monitor through an image inputting/outputting circuit 1144. At the same time, the image inputting/outputting circuit 1144 outputs image information outside the apparatus through an RBG output or video output. This information is captured as image information by the image capturing circuit 1133.

Recently, an improvement in diagnostic precision is expected by simultaneously obtaining pieces of diagnostic information based on a plurality of images according to the common medical image standard called DICOM (Digital Imaging and Communication in Medicine). According to this common standard, diagnostic images obtained by image diagnostic apparatuses of different types, e.g., a CT image diagnostic apparatus, MRI image diagnostic apparatus, and X-ray imaging apparatus, can be handled as data having the same data format.

In the ultrasound treatment apparatus according to this embodiment, for example, if the image capturing circuit 1133 is designed according to this DICOM, the B-mode image obtained by the ultrasound diagnostic apparatus and the diagnostic images obtained by other image diagnostic apparatuses can be simultaneously displayed on the same monitor. This allows the operator to compare and examine the images.

In addition, not only image information but also other data useful in treatment can be simultaneously displayed on the monitor of the ultrasound treatment apparatus according to the present invention through a computer network.

Figure 22:
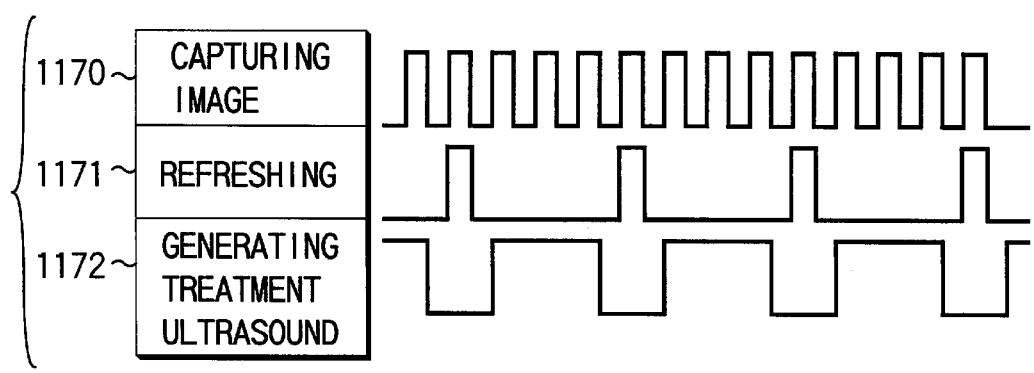
FIG. 22 is a timing chart showing the operation of the fourth embodiment.

FIG. 22 is a timing chart of the image capturing rate, display rate, and irradiation rate of the ultrasound treatment apparatus according to this embodiment. While no treatment ultrasound is irradiated (only a B-mode image is displayed), the image superimposing circuit 1131 superimposes treatment information on the B-mode image output from the image inputting/outputting circuit 1144 of the ultrasound diagnostic apparatus 1102, and the image display 1104 displays the resultant image. When treatment ultrasound is to be irradiated, the image capturing circuit 1133 of the ultrasound diagnostic apparatus is kept on.

The image capturing circuit 1133 captures diagnostic images corresponding to an ultrasound diagnostic image capturing rate 1170 in FIG. 22. When only intermittent display is to be performed, the image capturing circuit 1133 need not always capture diagnostic images and may capture images at an image display refreshing rate 1171 or treatment ultrasound irradiation rate 1172.

Treatment information is superimposed by the image superimposing circuit 1131. At this time, a treatment ultrasound generator irradiates treatment ultrasound corresponding to the treatment ultrasound irradiation rate 1172 from the treatment ultrasound source 1110. During irradiation of treatment ultrasound, noise components appear on diagnostic images, accompanying the irradiation. For this reason, an old diagnostic image is replaced with a newly captured diagnostic image during an OFF period of the treatment ultrasound irradiation rate 1172. That is, the information in the frame memory is replaced with new image information during an ON period of the image display refreshing rate 1171 in FIG. 22.

With this operation, no noise components appear on images upon irradiation of treatment ultrasound, and diagnostic images without any noise component can always be displayed. In addition, real-time diagnostic images can be displayed during periods other than treatment periods.

The display unit 1103, ultrasound treatment apparatus 1105, and ultrasound diagnostic apparatus 1102 are shown as separate blocks in FIG. 21. However, the same effect as that of the present invention can be obtained even if the display unit 1103 is incorporated in the ultrasound treatment apparatus 1105 or ultrasound diagnostic apparatus 1102.

In addition, according to the result obtained by tests conducted on animals by the present inventors, the intensity of echoes from a tumor displayed on a B-mode image gradually changes upon irradiation of ultrasound on the tumor. Each time an echo changes, almost completely uniform degeneration occurs in a focus region. If, therefore, initial changes in echo level in the process of uniform degeneration are monitored to stop irradiation, safe, reliable treatment can be realized. However, since initial changes in reflected echo level are very subtle, it is very difficult to determine by only visually checking an image a level at which a tumor uniformly degenerates.

Figures 23A, 23B:
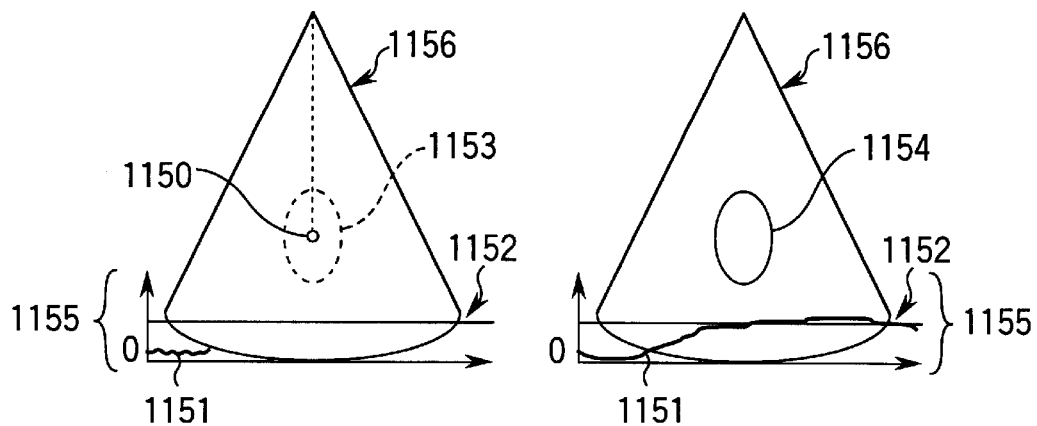
FIGS. 23A and 23B are views showing an example of display in the fourth embodiment.

FIG. 23A shows an example of image display before irradiation of treatment ultrasound. FIG. 23B shows an example of image display after irradiation of treatment ultrasound. In the displayed image in FIG. 23A, a B-mode image 1156, focal position 1150, and focus proximity range 1153 are displayed. At the same time, a intensity difference amount shift graph 1155 is displayed on a lower portion of the screen. On this intensity difference amount shift graph 1155, a intensity difference amount 1151 and threshold curve 1152 are displayed.

This ultrasound treatment apparatus obtains the difference between the average intensity, as an initial value, in the focus proximity range 1153 on the B-mode image 1156 before irradiation of treatment ultrasound and the average intensity near the focus on the B-mode image 1156 during intermittent irradiation of treatment ultrasound.

According to a method of obtaining this intensity difference, for example, an intensity signal corresponding to a reception echo level is extracted from an ultrasound transmitting/receiving circuit (not shown) for constructing the B-mode image 1156 at an ultrasound reception timing corresponding to the focus proximity range 1153. The average value of levels of one-frame component of this intensity signal is compared with the average value of a similar intensity signal that has been obtained before irradiation of treatment ultrasound. The difference between these average values is displayed as the intensity difference amount 1151 on the intensity difference amount shift graph 1155.

Note that the one-frame component does not indicate a one-frame component based on scanning lines constituting an image on, for example, a TV monitor, but "one frame" is formed when one raster operation at the start point of scanning is performed at the vibrator at the end point of scanning, provided that "one raster operation" is transmission/reception of ultrasound at one of many vibrators of the ultrasound probe which is located at the start point of scanning. These constructed frames are switched differently depending on the body tissue under examination whose B-mode image is to be obtained, and are properly selected in accordance with a direction from the operator or apparatus settings before operation.

If, for example, an internal organ that moves fast, e.g., a circulatory organ, is to be treated, a short transmission/reception period is assigned to one raster to shorten the total time required to construct one frame. This makes it possible to increase the number of frames per unit time. Therefore, the apparatus can satisfactorily follow the fast movement of, e.g., a cardiac valve.

FIG. 23B shows the image display operation of the ultrasound treatment apparatus after irradiation of treatment ultrasound. In contrast to the B-mode image 1156 before irradiation of treatment ultrasound, a hyper Echoic region 1154 is superimposed on the focus proximity range 1153 around the focal position 1150. This hyper Echoic region 1154 is produced because the tissue of the tumor at the focal position 1150 becomes degenerated protein. In the ultrasound treatment apparatus of this embodiment of the present invention, the difference between the average value of intensity information of the hyper Echoic region 1154 and the average value of intensity information before irradiation is displayed as the threshold curve 1152.

More reliable, uniform ultrasound irradiation treatment can be realized by control which stops irradiation of treatment ultrasound when the above difference exceeds a predetermined threshold. For example, irradiation of treatment ultrasound is stopped when a change in intensity difference amount indicated by the intensity difference amount shift graph 1155 exceeds the threshold curve 1152. This stop control can be realized by calculating the difference between captured intensity information and a predetermined threshold, and stopping the operation of a driving circuit (not shown) for generating treatment ultrasound on the basis of the difference.

Control may be performed such that irradiation of treatment ultrasound is automatically stopped when a change in intensity difference amount becomes below the threshold curve 1152. In addition, upper and lower thresholds may be set, and irradiation is stopped when the above change falls outside the range of the upper and lower thresholds. Alternatively, information (guide) of an irradiation stop is given to the operator to notify the operator of the end of treatment by, for example, generating a sound, performing display operation (e.g., blinking characters indicting the completion of irradiation), or vibrating the ultrasound applicator held by the operator with his/her hand.

Note that a region to be captured to calculate the average value of intensity information may be designated by a direction input by manually operating a trackball. Alternatively, this apparatus may additionally have the function of automatically setting a size by selecting data from location and range data as default values.

There are differences in intensity before irradiation of treatment ultrasound among patients owing to the symptoms, degrees of symptoms, and physical constitutions of the respective patients. To prevent the influences of such differences among individuals, an initial average intensity is normalized to a value determined on the basis of, e.g., statistical data and displayed on the screen, together with the threshold curve 1152. In this display form, intensity change information resistant to the influence of a difference among individuals can be given to the operator by displaying the process of changes in the intensity difference amount 1151 over time.

In the above embodiment, difference information associated with an original image before irradiation of treatment ultrasound is displayed on the basis of the information obtained by averaging intensity signals in the focus proximity range 1153 at the focal position 1150. However, an average intensity signal acquisition region may be set at a predetermined fixed position, and a value obtained at this position may be used. According to still another method, images corresponding to a plurality of frames are acquired when intermittent B-mode images are obtained, and intensity signals at the focal position 1150 are time-averaged, thereby displaying the resultant value.

In the ultrasound treatment apparatus of each embodiment of the present invention, an ultrasound image diagnostic apparatus is used as an image diagnostic apparatus. However, the present invention is not limited to this, and can be applied to the display/control operations of other image diagnostic apparatuses such as a CT apparatus, X-ray apparatus, and MRI apparatus.

Figure 24:
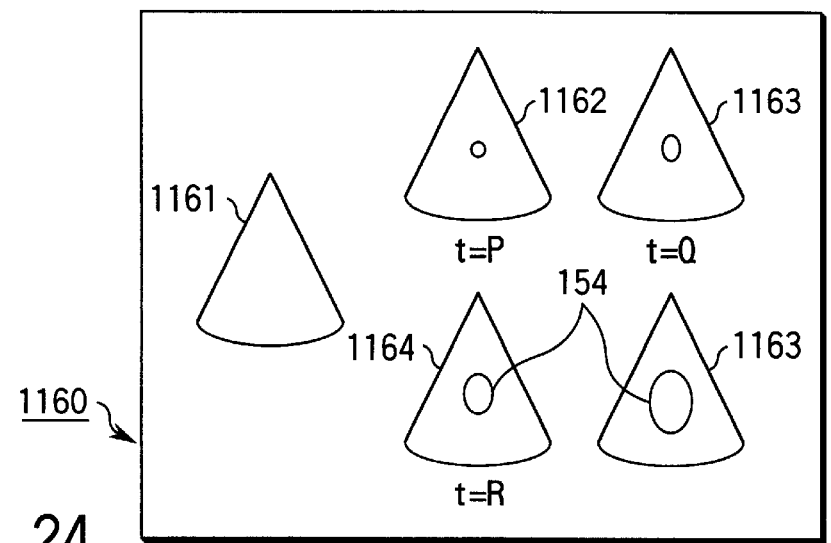
FIG. 24 is a view showing another example of display in the fourth embodiment.

FIG. 24 shows one example of a displayed image 1160, which is displayed on the monitor (not shown) of the ultrasound treatment apparatus according to the present invention. On this display image 1160, B-mode images of a tumor, which are captured by the ultrasound image diagnostic apparatus in time series are displayed. This display operation is performed to simultaneously display an initial B-mode image 1161, first process image 1162 obtained period t=P sec after irradiation of treatment ultrasound, second process image 1163 obtained t=Q sec after irradiation, third process image 1164 obtained t=R sec after irradiation, and latest B-mode image 1165.

The initial B-mode image 1161 is a B-mode image before irradiation of treatment ultrasound on a tumor. Time-series images from this initial image to the latest B-mode image 1165 as the current image are simultaneously displayed. As the tumor is irradiated with treatment ultrasound, the temperature of the focus portion rises, and the focus portion becomes degenerated protein. As a consequence, this portion becomes the hyper Echoic region 1154. This hyper Echoic region 1154 expands as an irradiation period elapses. For example, as shown in FIG. 24, the hyper Echoic region 1154 gradually expands in time series from the first process image 1162 to the latest B-mode image 1165.

By displaying a trend in image changes due to degeneration in time series, the progress of ultrasound treatment or its completion timing are clearly displayed for review by the operator. If, for example, a plurality of images are displayed with respect to an initial image, as shown in FIG. 24, while images other than the initial image are updated over time, the operator can grasp a trend in changes at a glance.

Note that the respective captured B-mode images can be displayed at predetermined time intervals. Alternatively, the elapsed time from the start of irradiation of treatment ultrasound to the current time may be divided into elapsed times at predetermined intervals, and the respective captured B-mode images can be displayed at the respective elapsed times.

In addition, the normal B-mode image display and image display of B-mode images captured in time series may be switched at arbitrary or predetermined time intervals. In this embodiment, B-mode images are displayed only in time series. However, instead of the image display shown in FIGS. 23A and 23B, a B-mode image during treatment and an image before irradiation of treatment ultrasound can be selectively displayed.

Each embodiment described above has exemplified the ultrasound treatment apparatus of focusing type. However, the effects unique to the present invention can be obtained even if the present invention is applied to an ultrasound treatment apparatus of a type other than the focusing type. In addition, the type of generating treatment ultrasound is not limited to the type of using vibrators having concave surfaces. For example, the same effect can be obtained by using a two-dimensional array of vibrators in the form of a flat plate. Alternatively, an electromagnetic induction type ultrasound source may be used.

In each embodiment described above, medical treatment of a tumor by using the thermal effect of ultrasound has been described as an example. However, similar effects can be obtained by applying the present invention to medical treatment of other target portions to obtain a dynamic effect or chemical effect.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound treatment apparatus comprising:
   an ultrasound source for generating treatment ultrasound which is focused;
   a driving circuit for driving said ultrasound source to generate treatment ultrasound from said ultrasound source; and
   a controller for determining a focus intensity (W/cm$^2$) of the treatment ultrasound and an irradiation period (sec) of the treatment ultrasound under a condition in which a frequency (MHz) of the treatment ultrasound is a predetermined value, so that an index obtained by a product of the focus intensity, the irradiation period and the frequency falls within an appropriate range from 6,000 (inclusive) to 40,000 (inclusive), and for controlling said driving circuit based on the determined focus intensity and irradiation period, a lower limit of the range being set to cause thermal degeneration in a tissue of a tumor, and an upper limit of the range being set to avoid cell destruction of the tissue of the tumor.

2. An apparatus according to claim 1, wherein said controller controls said driving circuit to cause said driving circuit to drive said ultrasound source under an irradiation condition in which the focus intensity becomes not more than 2,000 (W/cm$^2$).

3. An apparatus according to claim 1, further comprising a console for inputting at least one of the focus intensity and the irradiation period, said controller determining the other of the focus intensity and the irradiation period on the basis of the input one of the focus intensity and the irradiation period and a frequency of the treatment ultrasound such that the index falls within the appropriate range.

4. An apparatus according to claim 1, further comprising a console for inputting both the focus intensity and the irradiation period, and means for generating a warning when the index obtained from the input focus intensity, the input irradiation time, and a frequency of the treatment ultrasound falls outside the appropriate range.

5. An apparatus according to claim 1, further comprising a memory storing an appropriate range of the index for each internal organ.

6. An apparatus according to claim 1, further comprising display means for graphically displaying the range.

7. An ultrasound treatment apparatus comprising:
   an ultrasound source for generating treatment ultrasound which is focused;
   a driving circuit for driving said ultrasound source to generate treatment ultrasound from said ultrasound source; and
   a controller for determining a focus intensity (W/cm$^2$) of the treatment ultrasound and an irradiation period (sec) of the treatment ultrasound under a condition in which a frequency (MHz) of the treatment ultrasound is a predetermined value, so that an index obtained from a product of the focus intensity, the irradiation period and the frequency falls within a predetermined range, and for controlling said driving circuit based on the determined focus intensity and irradiation period, a lower limit of the range being set to cause thermal degeneration in a tissue of a tumor, and an upper limit of the range being set to avoid cell destruction of the tissue of the tumor.

8. An apparatus according to claim 7, comprising:
   said controller determining said condition to be in said range having said upper limit defined as a maximum focus intensity not causing cell destruction and said lower limit defined as a minimum focus intensity causing cell degeneration.

9. An apparatus according to claim 8, comprising:
   said controller determining said upper and lower limits based upon an internal organ being irradiated.

10. An ultrasound treatment apparatus comprising:
    an ultrasound source for generating treatment ultrasound which is focused;
    a driving circuit for driving said ultrasound source to generate treatment ultrasound from said ultrasound source; and
    a controller for controlling said driving circuit such that an index obtained by a product of a focus intensity (W/cm$^2$) of the treatment ultrasound, an irradiation period (sec) of the treatment ultrasound and a frequency (MHz) of the treatment ultrasound falls within a predetermined range, a lower limit of the range being set to cause thermal degeneration in a tissue of a tumor, an upper limit of the range being set to avoid cell destruction of the tissue of the tumor, two of the focus intensity, the irradiation period and the frequency being determined as predetermined requirements, and the other being determined by the controller.

* * * * *